(12) United States Patent
Carr et al.

(10) Patent No.: US 9,669,164 B2
(45) Date of Patent: Jun. 6, 2017

(54) FILTERING NEEDLE CAP HAVING A SLEEVE SEALING AROUND A NEEDLE

(71) Applicant: CARRTECH LLC, Dickerson, MD (US)

(72) Inventors: Sue E. Carr, Dickerson, MD (US); Jessie Delgado, Durham, NC (US); Edward Browka, Oneida, NY (US); Charles E. McCall, Jr., Fuquay-Varina, NC (US); David L. Foshee, Apex, NC (US)

(73) Assignee: CARRTECH LLC, Dickerson, MD (US)

( * ) Notice: Subject to any disclaimer, the term of this patent is extended or adjusted under 35 U.S.C. 154(b) by 0 days.

(21) Appl. No.: 14/942,876

(22) Filed: Nov. 16, 2015

(65) Prior Publication Data

US 2016/0067410 A1    Mar. 10, 2016

Related U.S. Application Data

(63) Continuation of application No. PCT/US2014/038625, filed on May 19, 2014.
(Continued)

(51) Int. Cl.
*A61M 5/31* (2006.01)
*A61M 5/32* (2006.01)
(Continued)

(52) U.S. Cl.
CPC .......... *A61M 5/3145* (2013.01); *A61M 5/165* (2013.01); *A61M 5/32* (2013.01); *A61M 5/3202* (2013.01); *A61M 5/343* (2013.01)

(58) Field of Classification Search
CPC .. A61M 5/1782; A61M 5/329; A61M 5/3145; A61M 5/344
See application file for complete search history.

(56) References Cited

U.S. PATENT DOCUMENTS 2,626,603 A    1/1953   Gabriel
2,689,564 A    9/1954   Adams
(Continued)

OTHER PUBLICATIONS

Around (definitions 2[c] and 3[a])—Merriam-Webster Dictionary. Accessed online Sep. 9, 2016.*
(Continued)

*Primary Examiner* — Bhisma Mehta
*Assistant Examiner* — Matthew A Engel
(74) *Attorney, Agent, or Firm* — Kevin E. Flynn; Flynn IP Law

(57) ABSTRACT

A filtered needle for use in administering a liquid payload, including a needle and connector portion and a filtering needle cap. The filtering needle cap including a distal open end in fluid communication via an internal channel with a proximal open end of the filtering needle cap. The filtering needle cap proximal end sized to receive the distal end of the hub within the proximal end of the filtering needle cap to reversibly engage the hub when needle distal end is inserted into the internal channel. The filtering needle cap including a filter element and a seal to seal around an outside diameter of the hollow needle so that liquid payload is drawn into the lumen in the hollow needle as liquid payload is filtered and drawn into the fluid fitting. The filtering needle cap is designed to limit a dead volume of liquid payload drawn into the filtering needle cap but not entering into the distal end of the hollow needle.

18 Claims, 22 Drawing Sheets

Related U.S. Application Data

(60) Provisional application No. 61/824,486, filed on May 17, 2013, provisional application No. 61/910,149, filed on Nov. 29, 2013.

(51) Int. Cl.
*A61M 5/165* (2006.01)
*A61M 5/34* (2006.01)

(56) References Cited

U.S. PATENT DOCUMENTS

| | | | |
|---|---|---|---|
| 2,775,240 A | 12/1956 | Morrisey, Jr. | |
| 2,827,081 A | 3/1958 | Little | |
| 2,833,281 A | 5/1958 | Krug | |
| 2,857,913 A | 10/1958 | Miskel | |
| 2,864,366 A | 12/1958 | Miskel | |
| 2,876,770 A * | 3/1959 | White | A61M 5/326 604/198 |
| 2,972,991 A | 2/1961 | Burke | |
| 3,008,570 A | 11/1961 | Roehr | |
| 3,052,241 A * | 9/1962 | Myerson et al. | A61M 5/344 604/192 |
| 3,757,780 A * | 9/1973 | Ishikawa | A61M 5/3145 604/190 |
| 4,127,131 A * | 11/1978 | Vaillancourt | A61M 5/165 210/448 |
| 4,137,917 A | 2/1979 | Cohen | |
| 4,180,071 A * | 12/1979 | Oiwa | A61M 5/32 604/190 |
| 4,273,123 A * | 6/1981 | Lemelson | A61M 5/3213 604/110 |
| 4,316,462 A * | 2/1982 | Baker | A61M 5/1782 604/190 |
| 4,365,626 A * | 12/1982 | House | A61M 5/002 604/190 |
| 4,617,012 A * | 10/1986 | Vaillancourt | A61M 39/10 285/12 |
| 4,725,267 A * | 2/1988 | Vaillancourt | A61M 5/3202 604/192 |
| 4,747,831 A * | 5/1988 | Kulli | A61M 5/322 604/110 |
| 4,795,432 A * | 1/1989 | Karczmer | A61M 5/3257 604/110 |
| 4,887,998 A * | 12/1989 | Martin | A61B 5/1438 604/110 |
| 4,927,416 A * | 5/1990 | Tomkiel | A61M 5/315 604/198 |
| 4,935,016 A * | 6/1990 | Deleo | A61M 5/3271 604/198 |
| 4,998,924 A * | 3/1991 | Ranford | A61M 5/3271 604/110 |
| 5,059,185 A * | 10/1991 | Ryan | A61M 5/3243 600/576 |
| 5,064,418 A | 11/1991 | Cronin | |
| 5,080,648 A * | 1/1992 | D'Antonio | A61M 5/2425 604/135 |
| 5,156,599 A * | 10/1992 | Ranford | A61M 5/3271 128/919 |
| 5,158,550 A | 10/1992 | Scholl, Jr. | |
| 5,295,963 A * | 3/1994 | Deeks | A61M 5/3257 604/110 |
| 5,312,370 A * | 5/1994 | Talonn | A61M 5/3271 604/197 |
| 5,338,310 A * | 8/1994 | Lewandowski | A61B 5/1438 604/110 |
| 5,601,536 A * | 2/1997 | Crawford | A61M 25/0618 604/166.01 |
| 5,674,203 A * | 10/1997 | Lewandowski | A61B 5/1438 128/919 |
| 5,735,823 A * | 4/1998 | Berger | A61M 5/3243 604/192 |
| 5,746,727 A * | 5/1998 | Graves | A61M 25/0631 604/198 |
| 5,795,336 A * | 8/1998 | Romano | A61M 5/3271 604/110 |
| 5,879,337 A * | 3/1999 | Kuracina | A61M 5/3243 604/192 |
| 6,287,278 B1 * | 9/2001 | Woehr | A61M 25/0618 604/110 |
| 6,302,868 B1 * | 10/2001 | Mohammad | A61B 5/1438 604/192 |
| 6,623,458 B2 * | 9/2003 | Woehr | A61M 5/3273 128/919 |
| 6,629,959 B2 * | 10/2003 | Kuracina | A61B 5/1411 604/192 |
| 6,629,962 B2 | 10/2003 | Correa | |
| 6,679,864 B2 * | 1/2004 | Gagnieux | A61M 5/326 604/110 |
| 6,749,588 B1 * | 6/2004 | Howell | A61M 5/3273 604/110 |
| 6,776,775 B1 * | 8/2004 | Mohammad | A61B 5/150572 604/195 |
| 6,860,871 B2 * | 3/2005 | Kuracina | A61B 5/1411 604/192 |
| 6,958,055 B2 * | 10/2005 | Donnan | A61J 1/2096 600/573 |
| 7,306,740 B2 * | 12/2007 | Freund | A61B 17/32002 210/781 |
| 7,632,243 B2 * | 12/2009 | Bialecki | A61M 25/0618 604/110 |
| D623,732 S * | 9/2010 | Brady | D24/113 |
| 7,811,261 B2 * | 10/2010 | Rubinstein | A61M 5/326 604/198 |
| 7,927,314 B2 * | 4/2011 | Kuracina | 604/110 |
| 8,002,751 B2 | 8/2011 | Carr | |
| 8,162,882 B2 * | 4/2012 | Rubinstein | A61M 5/326 604/110 |
| RE43,473 E * | 6/2012 | Newby | A61B 5/1438 604/110 |
| 8,568,367 B2 * | 10/2013 | Griffiths | A61M 5/2033 604/190 |
| 2005/0277893 A1 * | 12/2005 | Liversidge | A61M 5/31501 604/198 |
| 2009/0227950 A1 * | 9/2009 | Jensen | A61M 5/326 604/110 |
| 2010/0042053 A1 * | 2/2010 | Dillard, III | A61M 5/3257 604/198 |
| 2011/0319817 A1 * | 12/2011 | Rubinstein | A61M 5/326 604/110 |
| 2012/0289930 A1 * | 11/2012 | Rubinstein | A61M 5/326 604/506 |
| 2014/0261877 A1 * | 9/2014 | Ivosevic | A61J 1/2096 141/27 |
| 2016/0317389 A1 * | 11/2016 | Ivosevic | A61J 1/2096 |

OTHER PUBLICATIONS

Inho, Han, Patent Cooperation Treaty International Search Report & Written Opinion of the International Searching Authority for PCT Application PCT/US2014/038625 (parent application to this application), Oct. 10, 2014, 16 pages, Korean Intellectual Property Organization.

Yang, Woong Chul, Patent Cooperation Treat International Preliminary Report on Patentability for PCT Application No. PCT/US2014/038625 (parent application to this application), Sep. 3, 2015, 12 pages, Korean Intellectual Property Organization.

19 Gauge×⅞ inch High Flow Filter Needle with 5 Micron Filter and Guard, downloaded from http://us.bbraunoem.com/cps/rde/xchag/oem-bbraunoem-en-us/hs.xsl/products.html?id-000207 on May 28, 2014, Published by B. Braun Medical Inc.

Filter Needles, downloaded from http://www.bbraunusa.com/products.html?prid=PRID00006974 on May 28, 2014, Published by B. Braun Medical Inc.

BD-Blunt-Fill-and-Blunt-Filter-Needles downloaded from http;//www.bbraunusa.com on May 28, 2014, 1 page, Published by B. Braun Medical Inc.

(56) References Cited

OTHER PUBLICATIONS

Fluid Filtration Filter Straw downloaded from http://www.allegromedical.com//infusion-iv-supplies-c6448/filtered-medication-transfer-device on May 28, 2014, Allegro Medical Supplies Inc.
Filter Needle (100 Needles) downloaded from http://medidose.com/filterneedle100needles.aspx on May 28, 2014 (copyright 2010) The Medi-Dose Group.
Filter Straw(R), brochure downloaded from B. Braun metadate indicates creation Dec. 15, 2008, downloaded May 28, 2014, 2 pages, Published by B. Braun Medical Inc.
Monoject(TM) Filter Needles with Polypropylene Hub, web page http://www.medline.com/jump/product/x Z05-PF30481 downloaded on May 28, 2014 (enlarged image appended to end for convenience of Office), published by Medline Industries, Inc.

\* cited by examiner

10

610

<u>10</u>

10

510

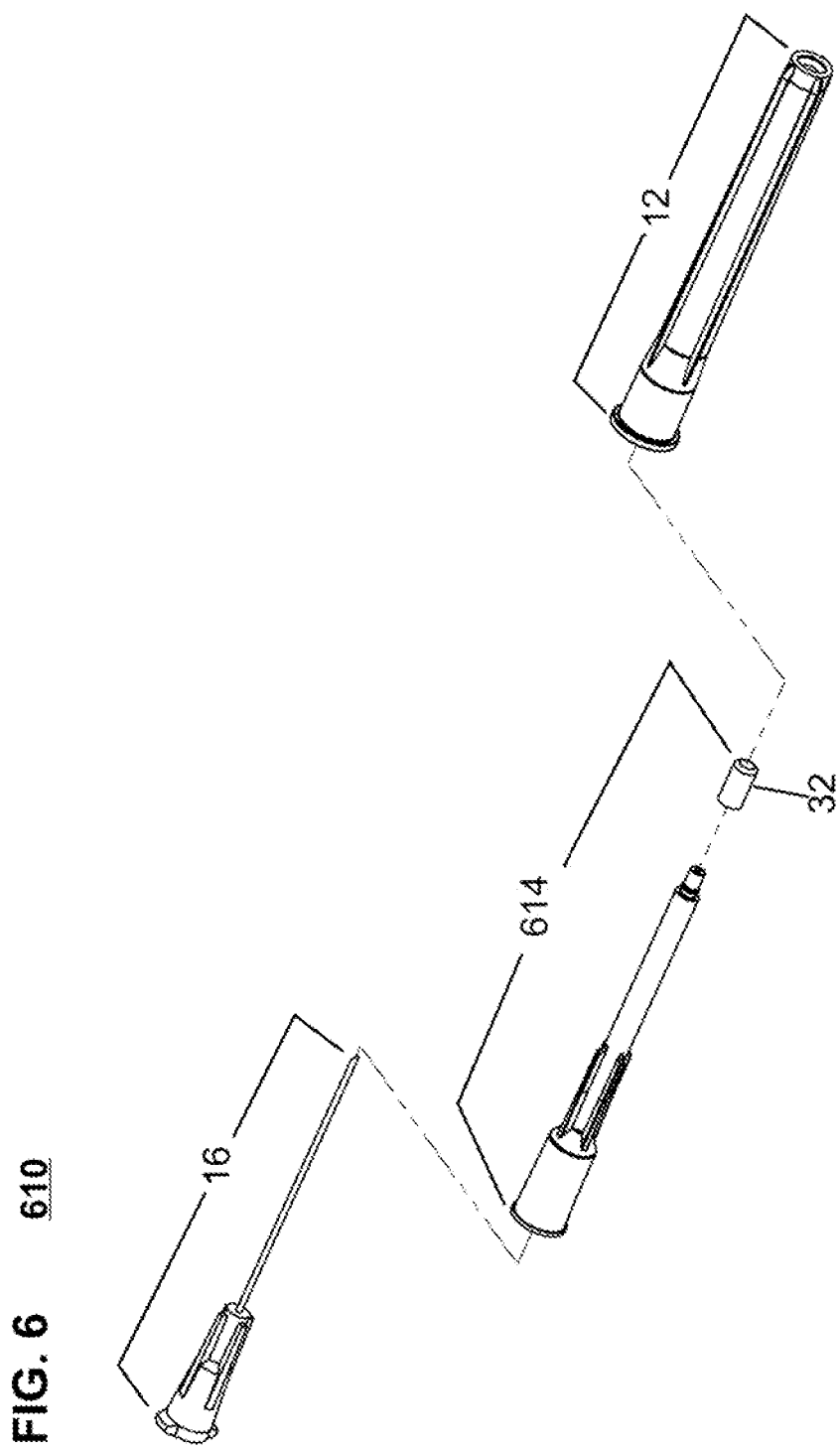

610

610

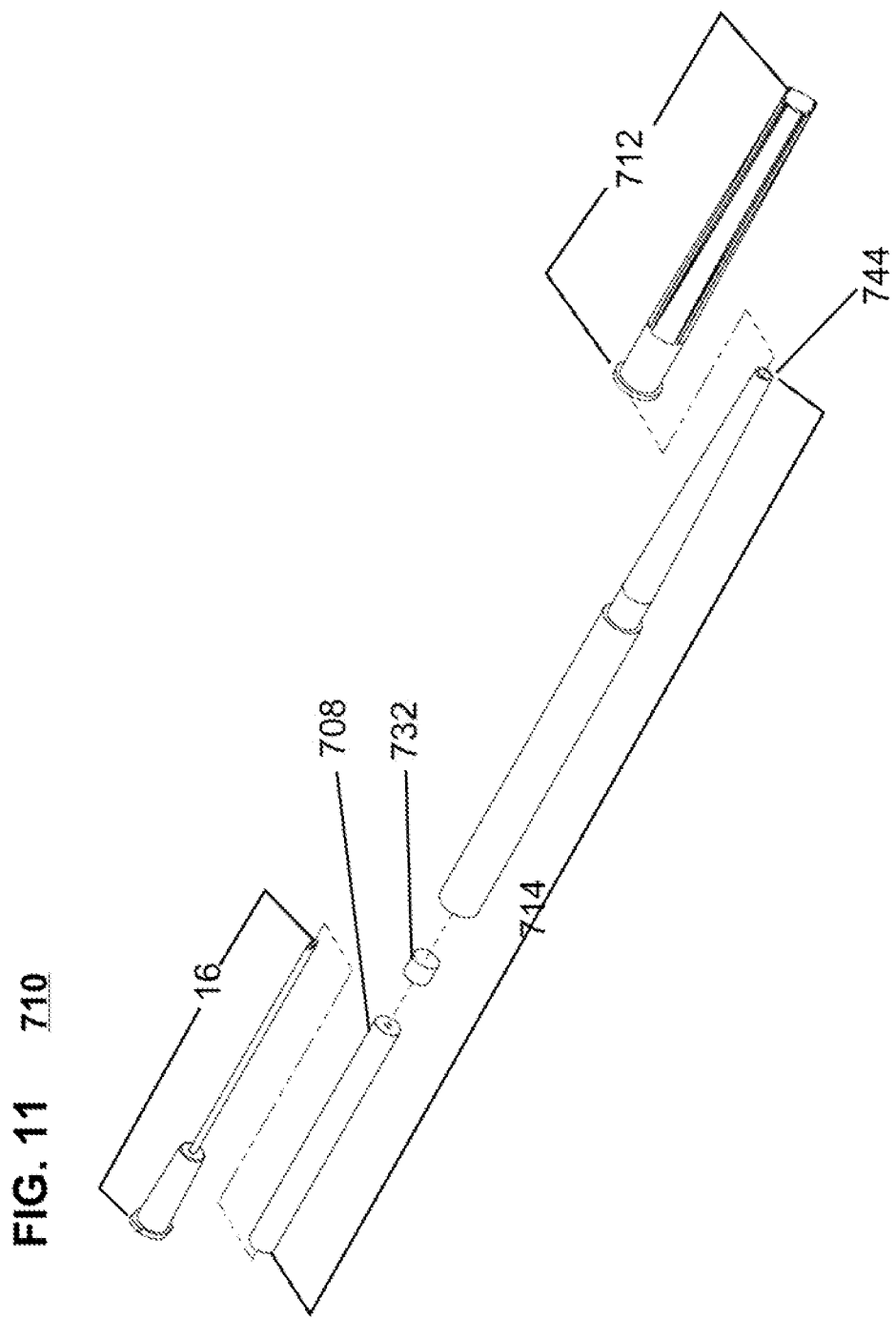

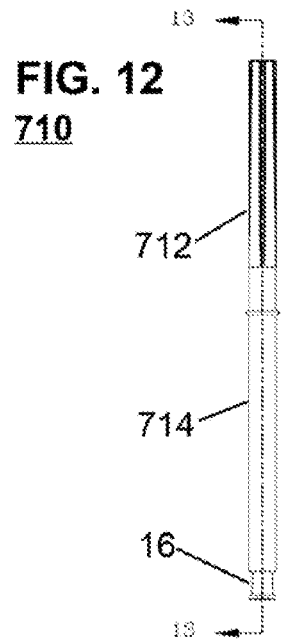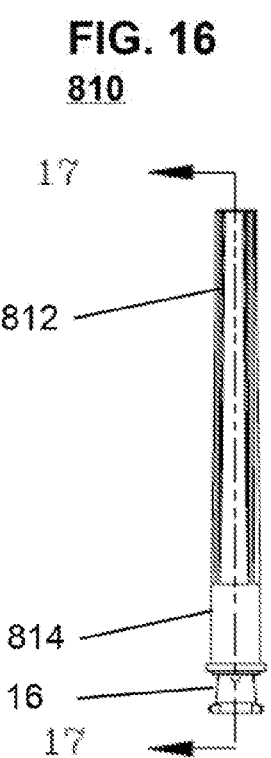

710

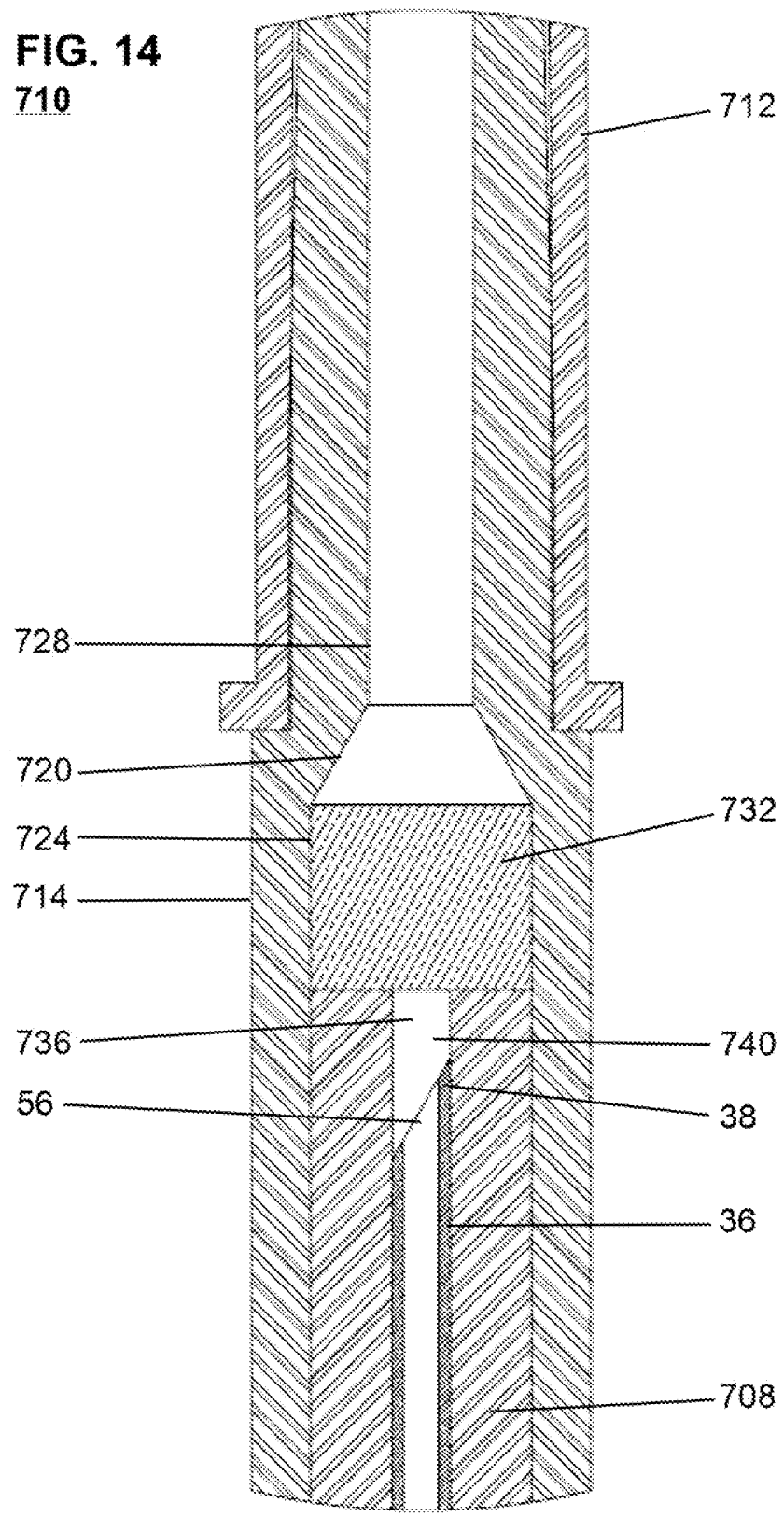

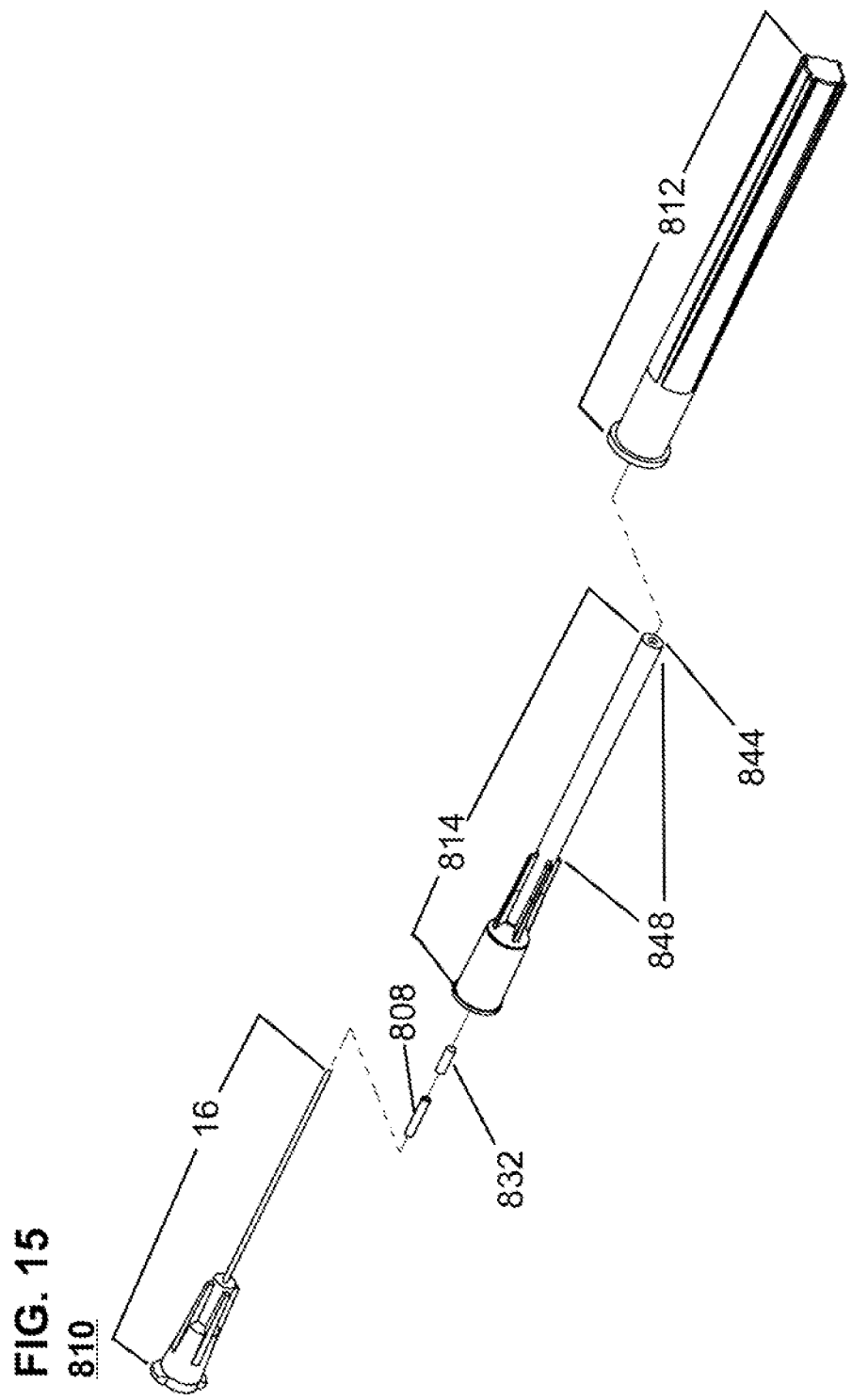

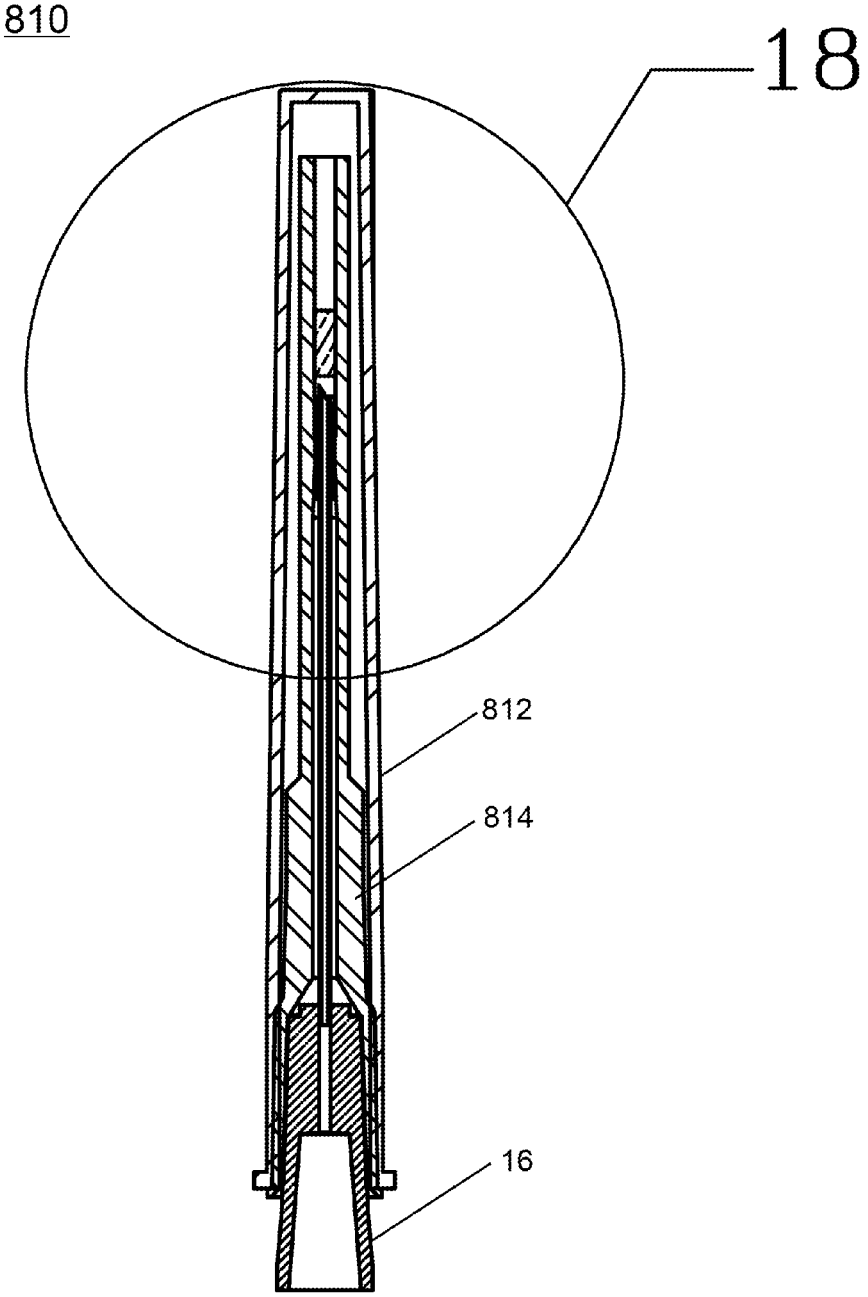

810

310

910

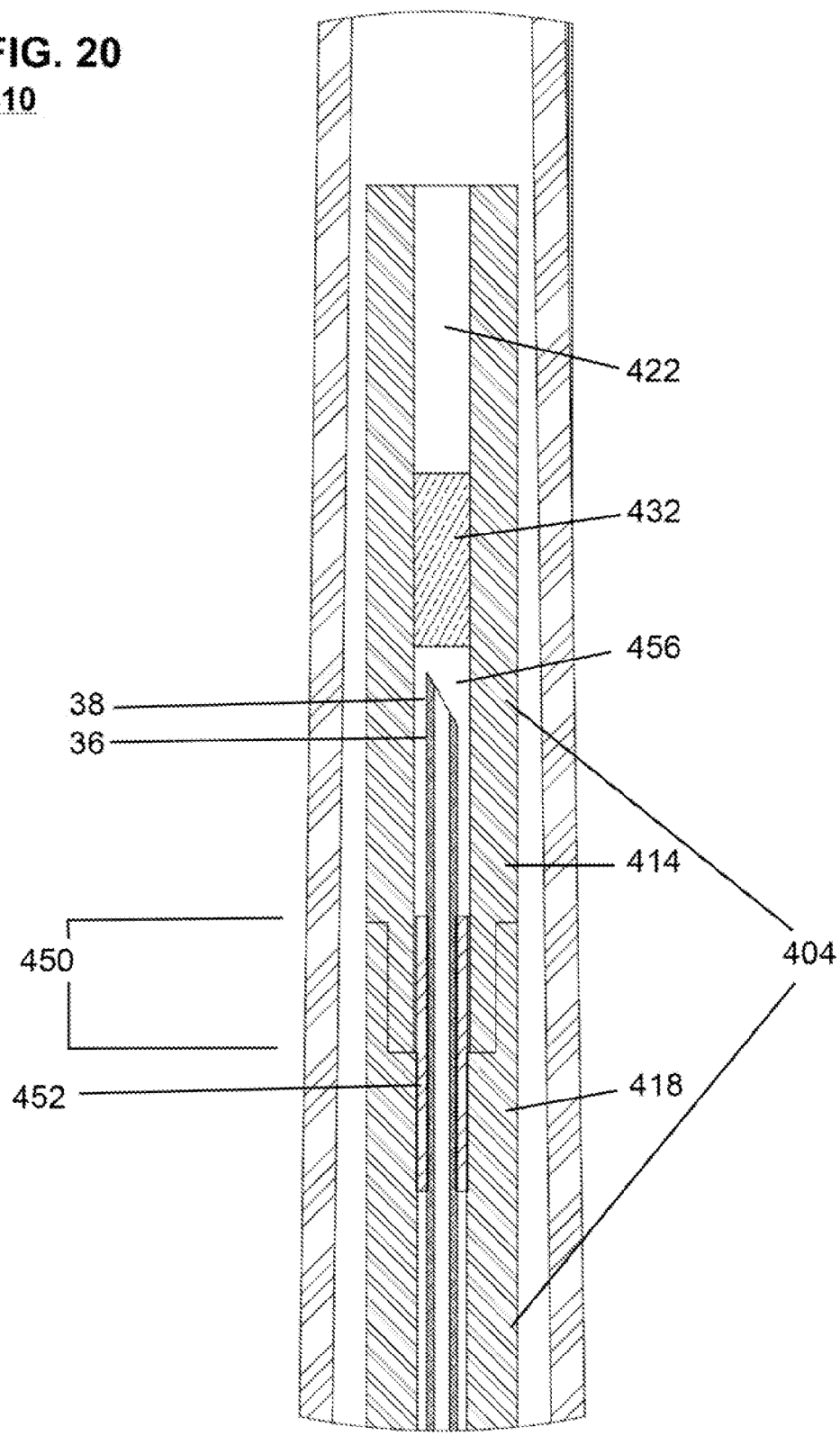

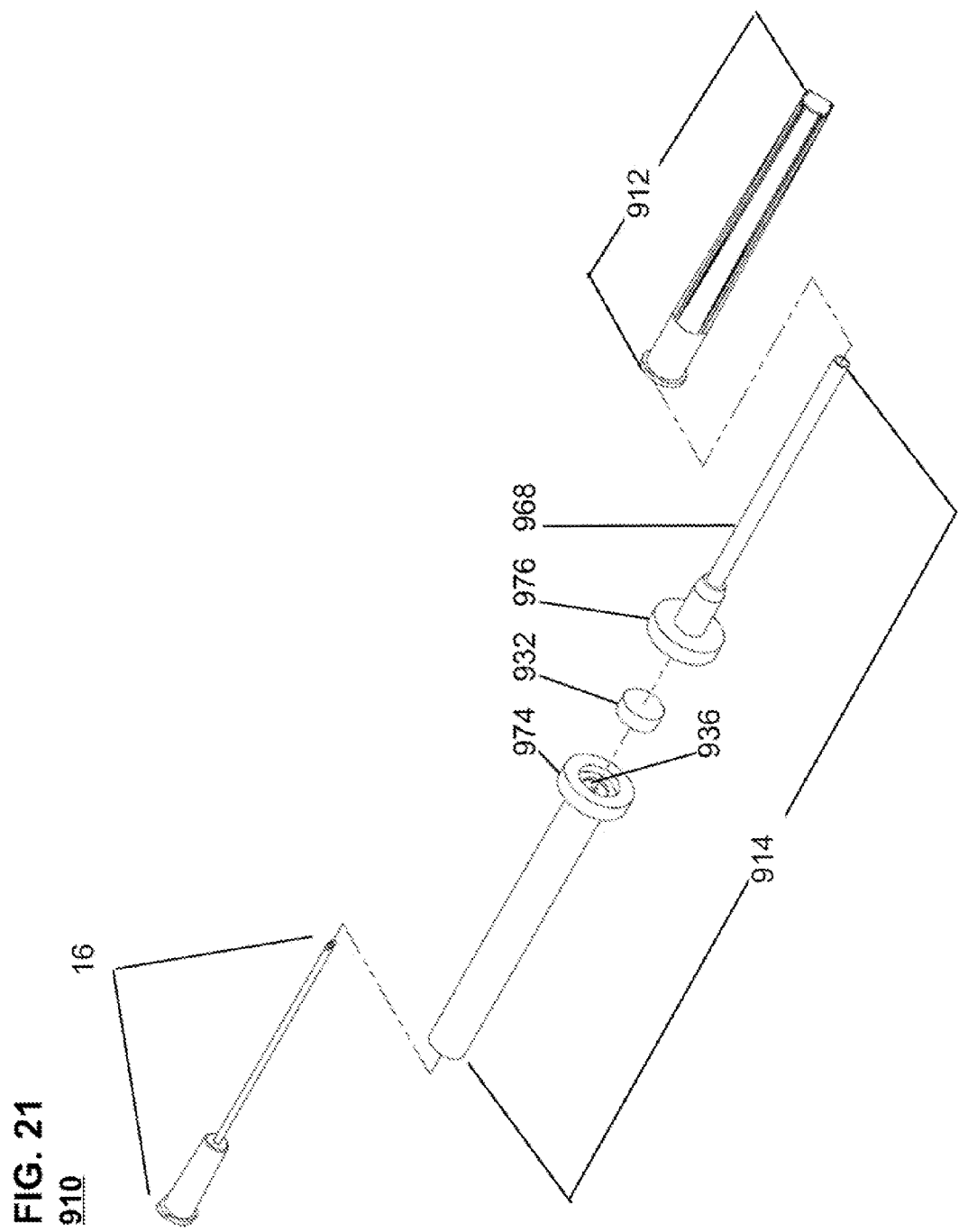

<u>910</u>

910

FILTERING NEEDLE CAP HAVING A SLEEVE SEALING AROUND A NEEDLE

This application incorporates by reference and claims priority to co-pending Patent Cooperation Treaty Application No. PCT/US2014/038625 filed May 19, 2014 for Filtering Needle Cap. The current application claims through the '625 application the benefit of a pair of provisional applications: U.S. Provisional Patent Application No. 61/824,486 filed May 17, 2013 for Filter Needle Cap; and U.S. Provisional Patent Application No. 61/910,149 filed Nov. 29, 2013 for Filtered Needle, both of which are incorporated by reference. Likewise, U.S. Pat. No. 8,002,751 issued Aug. 23, 2011 for Filter Needle is incorporated by reference. While these applications have been incorporated by reference to provide additional detail it should be noted that these other applications were written at an earlier time and had a different focus from the present application. Thus, to the extent that the teachings or use of terminology differ in any of these incorporated applications from the present application, the present application controls.

BACKGROUND

Field of the Disclosure

This disclosure relates generally to a filtered needle for safely administering pharmaceuticals or other liquid payloads needing filtration before administration to a patient. The filtered needle may be used with human patients, veterinary uses for animals, and other uses that benefit from the filtering of a liquid payload before delivery. In this disclosure and the claims that follow, the term needle should be understood as a hypodermic needle or analogous needle with an open distal end and an interior lumen to allow for movement of a liquid.

Liquid pharmaceuticals are typically stored in sealed glass ampoules (often spelled ampule) or other known storage devices. In the case of glass ampoules, order to gain access to the pharmaceuticals, the ampoule is opened by snapping the glass neck. In so doing, debris in the form of glass shards may be produced. The shards must be removed from the pharmaceuticals prior to administration. The debris is typically removed by drawing up the pharmaceutical through a filtered cannula or straw secured to the end of the syringe.

While the most common use of a syringe to deliver liquids is to deliver a liquid pharmaceutical, other liquid payloads can be drawn in from a reservoir through a filter to remove debris before delivering the filtered liquid payload through a needle connected to the syringe.

Examples of uses beyond pharmaceuticals include the injection of some nutraceuticals into a patient. Some public health organizations provide needle exchanges to people addicted to illegal drugs as a way to limit spread of disease and a filtered needle may be of benefit in this application. Some blood products such as PCC (Prothrombin Complex C) use a filtered needle. The list of uses should not be deemed a limitation to the scope of the claims as those of skill in the art will be able to adapt the teachings of the present disclosure for use with a particular liquid payload and need for filtration.

Methods for removing debris include a two stage process and a one stage process. In the two stage process, a needle or straw has a filter element secured in the needle and connector portion. As the liquid payload is drawn up into the syringe, the filter traps the debris removing it from the liquid payload to be administered. The filtered straw or needle is then removed from the syringe and discarded. In order to avoid inadvertent administration of contaminated liquid payload to the patient care must be taken to remove and discard the filtered needle. In addition to the danger of mistakenly administering a contaminated liquid payload to a patient, the two stage process may involve the use of specially adapted and costly disposable devices.

U.S. Pat. No. 8,002,751 for Filter Needle discloses a one-step process. This one step process employs a specially fabricated frangible needle or straw which has a filter secured near the inlet. The needle or straw has a score line between the filter and the syringe connection. The pharmaceutical is first drawn up from the ampoule through the filter trapping the debris. The tip of the needle or straw is then snapped off along the score line and discarded, taking with it the filter and trapped debris. The one stage process requires a specially fabricated needle or straw which may be snapped off leaving a sharp end for administering the pharmaceuticals. It is difficult to manufacture a needle having the required properties. In addition, questions have been raised as to whether a frangible needle or straw may be produced which does not itself produce debris, such as metal or plastic shards.

Accordingly, an inexpensive and reliable system for filtering liquid payloads before delivery is desired.

VOCABULARY

Proximal & Distal.

The terms proximal and distal are commonly used when discussing medical devices. For the purposes of this application and the claims that follow, proximal means the end that is normally held by the user and distal is the opposite end. This in the case of a hypodermic needle, the end of the needle injected into the patient would be the distal end and the end manipulated by the user would be the proximal end.

Chamber.

The term chamber is used below in order to describe portions of an interior pathway through which the liquid payload travels. While in some uses of the word chamber, the chamber may be sealed by closing doors (such as a bed chamber or the judge's chamber), in this context, a chamber is a partially enclosed space having an ingress and egress.

Seal.

In the present disclosure and the claims that follow, the term seal is used as the teachings of the present disclosure call for creating a seal between the outer perimeter of the needle and the inner perimeter of a cannula within the filtering needle cap so that the syringe may effectively draw the liquid payload through the interior of the needle without pulling air past the seal and into the open distal end of the needle. A seal adequate for this purpose may not be a sufficient seal to maintain a more dramatic pressure differential across the seal or maintain a seal against a more moderate pressure gradient for a substantial period of time. Thus, in this context, the noun and verb seal indicates a seal sufficient to allow the filtering needle cap to seal around the outer diameter of the needle to allow the syringe to draw in liquid payload.

SUMMARY OF THE DISCLOSURE

Aspects of the teachings contained within this disclosure are addressed in the claims submitted with this application upon filing. Rather than adding redundant restatements of the contents of the claims, these claims should be considered incorporated by reference into this summary.

Some aspects of the present disclosure may be expressed as a filtered needle for use in administering a liquid payload, the filtered needle including a needle and connector portion and a filtering needle cap. The needle and connector portion including: a hollow needle with a needle distal end having an opening to a lumen running through the hollow needle; and a hub. The hub including an open proximal end adapted to reversibly engage a fluid fitting and; a distal end of the hub engaged with a proximal end of the hollow needle. The filtering needle cap including a distal open end in fluid communication via an internal channel with a proximal open end of the filtering needle cap. The filtering needle cap proximal end sized to receive the distal end of the hub within the proximal end of the filtering needle cap to reversibly engage the hub when needle distal end is inserted into the internal channel. The filtering needle cap including a filter element adapted for removing debris from the liquid payload as the liquid payload is drawn through the filtering needle cap into the lumen within the hollow needle as liquid payload is drawn into the fluid fitting. The filtering needle cap including a seal to seal around an outside diameter of the hollow needle so that liquid payload is drawn into the lumen in the hollow needle as liquid payload is drawn into the fluid fitting.

The seal may be placed towards the distal end of the hollow needle so that the distal end of the seal is closer to the distal end of the hollow needle than to the proximal end of the hollow needle. The distal end of the seal may be distal to a proximal end of the opening to the lumen running through the hollow needle.

Other aspects of the present disclosure may be expressed as a method for loading a quantity of filtered liquid payload into a syringe and connected hollow needle. The method including the steps of using a syringe to draw in liquid payload from a reservoir of liquid payload, the liquid payload passing through a filter element in a filtering needle cap before entering an opening in a needle distal end before removing the filtering needle cap from the filtered needle to expose the needle distal end.

The filtered needle may have a seal. The seal may be placed towards the distal end of the hollow needle so that the distal end of the seal is closer to the distal end of the hollow needle than to the proximal end of the hollow needle. The distal end of the seal may be distal to a proximal end of the opening to the lumen running through the hollow needle.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provide below as one of skill in the art will recognize that inventive concepts illustrated in various examples can be combined together in order to address a specific application.

Other systems, methods, features and advantages of the disclosed teachings will be or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIG. 6 is an exploded perspective view of a filtering needle cap according to another claimed embodiment.

FIG. 11 is an exploded perspective view of a filtering needle cap according to another claimed embodiment.

FIG. 12 is an elevation of the arrangement of FIG. 11 in assembled form.

FIG. 14 is a fragmentary enlargement of the filter tip within circular arrow 14 shown in FIG. 13.

FIG. 15 is an exploded perspective view of a filtering needle cap according to another claimed embodiment.

FIG. 16 is an elevation of the arrangement of FIG. 15 in assembled form.

FIG. 17 is a sectional illustration of the filtering needle cap taken along line 17-17 of FIG. 16.

FIG. 20 shows a portion of a filter tip to highlight the use of a two-part straw.

FIG. 21 is an exploded perspective view of a filtering needle cap according to another claimed embodiment.

DETAILED DESCRIPTION

The set of figures in FIG. 1 through FIG. 5 illustrate an embodiment of a filtered needle 10.

Figure 1:
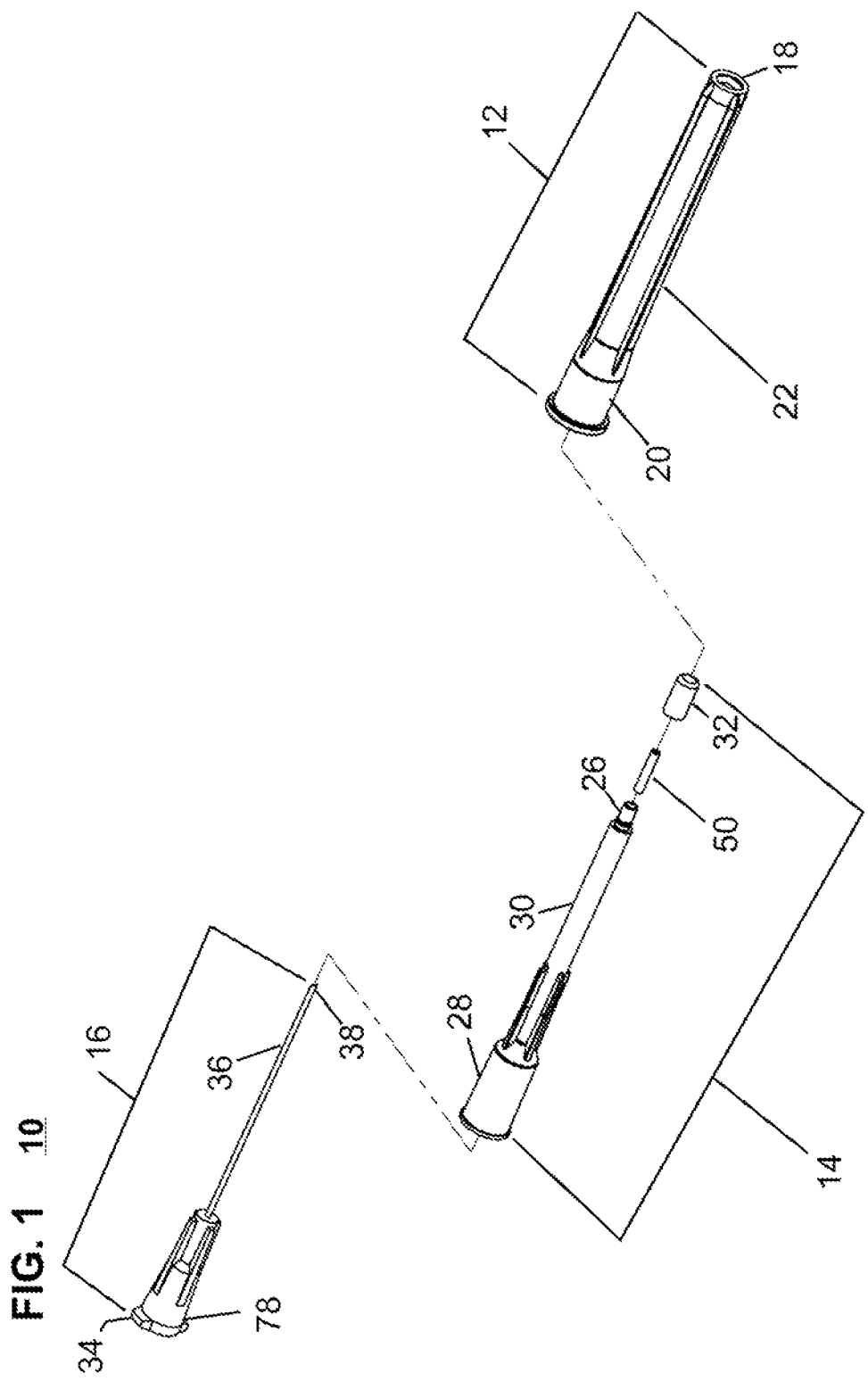
FIG. 1 is an exploded perspective view of a filtering needle cap according to a claimed embodiment.
Figure 2:
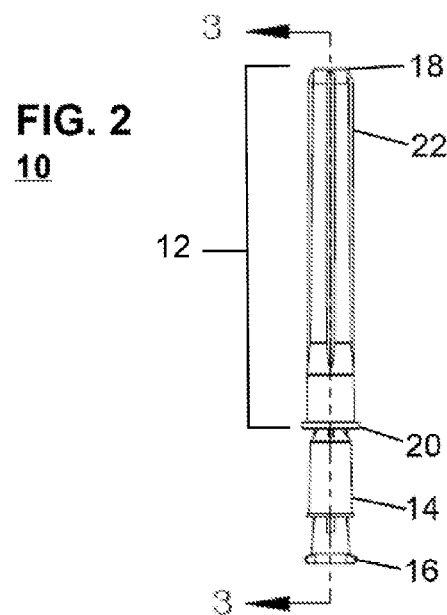
FIG. 2 is an elevation of the arrangement of FIG. 1 in assembled form.
Figure 7:
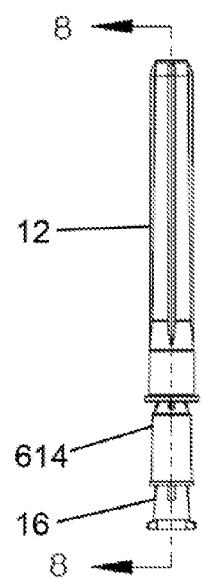
FIG. 7 is an elevation of the arrangement of FIG. 6 in assembled form.
Figure 3:
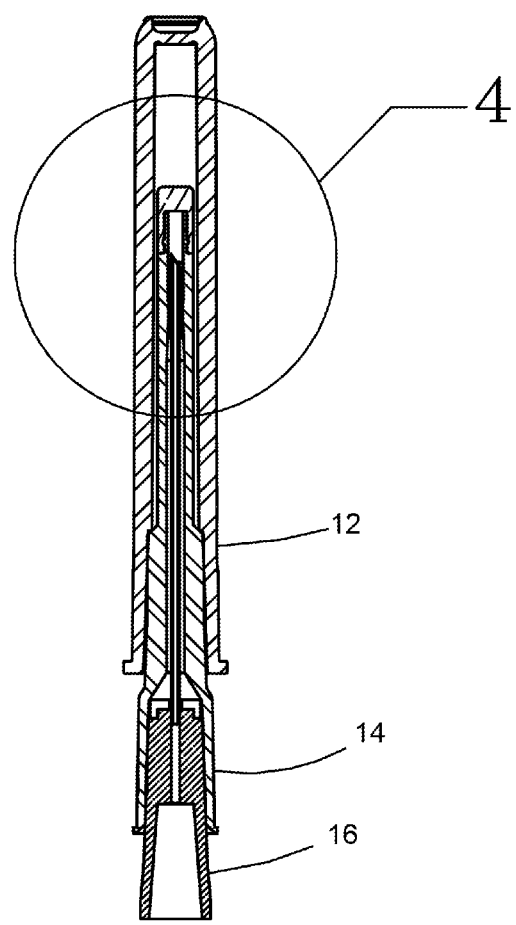
FIG. 3 is a sectional drawing taken along line 3-3 of FIG. 2.
Figure 4:
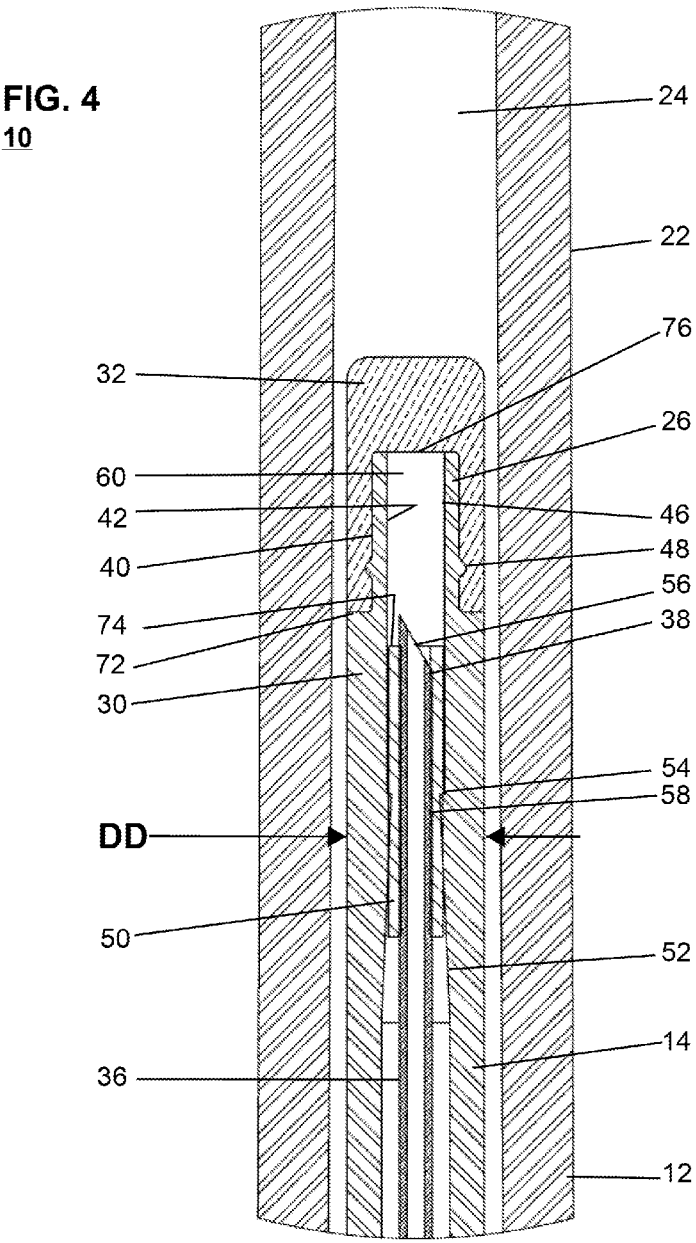
FIG. 4 is a fragmentary enlargement of the filter tip within circular arrow 4 shown in FIG. 3.
Figure 5:
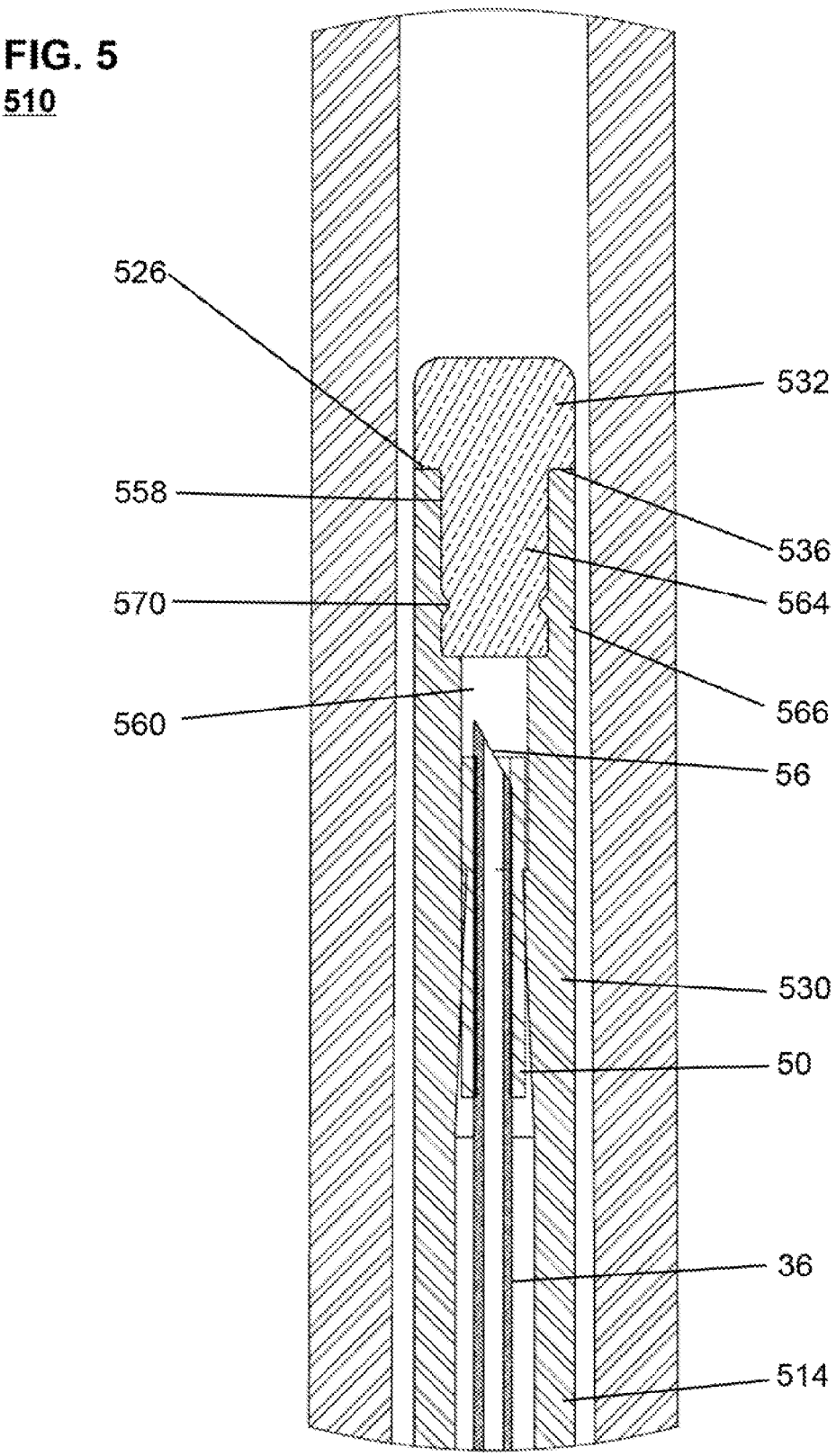
FIG. 5 is a fragmentary enlargement of an alternative embodiment of the filter tip shown in FIG. 4.

FIG. 1 illustrates the filtered needle 10 in exploded perspective form. FIG. 2 is an elevation of the embodiment of FIG. 1 in a fully assembled form, for example, in condition for shipping. FIG. 3 and FIG. 4 illustrate sectional and enlarged views of components of the filtered needle 10. FIG. 5 is an enlargement of an alternative embodiment of the arrangement shown in FIG. 4.

The filtered needle 10 includes an outer cap 12, a filtering needle cap 14 coaxially disposed within the outer cap 12 and a needle and connector portion 16 coaxially disposed within the filtering needle cap 14. The outer cap 12 has a closed distal end 18, a proximal portion 20 which is open and an intermediate section 22 having an inner chamber 24 (see FIG. 4) for receiving the filtering needle cap 14 therein. FIG. 1 uses brackets to indicate the scope of the major portions (12, 14, and 16) of the filtered needle 10. Subsequent figures use simple lead lines to minimize clutter in the drawings set.

The filtering needle cap 14 has a distal portion 26 which is open; a proximal portion 28 which is also open. The filtering needle cap 14 may be secured concentrically within the proximal portion 20 of the outer cap 12. The filtering needle cap 14 has an intermediate portion 30 which is hollow and extends into the intermediate section 22 of the outer cap 12. A filter element 32 is secured to the distal portion 26 of the intermediate portion 30.

The needle and connector portion 16 has a proximal end 34 which may be in the form of a hub 78 secured within the open proximal portion 28 of the filtering needle cap 14. The hub 78 may be adapted to work with a Luer fitting sometimes called a Luer Taper and defined in ISO 594 Standards. Luer fittings include those known as Luer-Lock and Luer-Slip (sometimes slip tip). While various Luer fittings are very common connection for medical devices, the teachings of the present disclosure are not limited to any specific fitting as other connections could be used.

Frequently, but not always, the connection between the needle and the hub 78 is augmented by an adhesive component. Such an adhesive component is conventional and not a point of focus for the present disclosure. Thus, details of this adhesive component are not provided. The adhesive component may be considered a part of the hub 78 for the purposes of this disclosure and the claims that follow.

A hollow needle 36 is secured to the proximal end 34 of the needle and connector portion 16 and extends axially within the intermediate portion 30 of the filtering needle cap 14 towards the distal portion 26. The needle 36 has a distal end 38.

FIG. 4 illustrates a more detailed enlarged view of a distal end of the filtering needle cap 14. As noted previously, the filter element 32 is secured to the distal portion 26 of the filtering needle cap 14. The distal portion 26 has an outer wall 40 with outward projections 48 to retain the filter element 32 by engaging with the inner wall 46 of the filter element 32. A shoulder 72 separates the filtering needle cap 14 distal portion 26 from the filtering needle cap 14 intermediate portion 30

Filter element 32 has an inner wall 46 which mates with the outer wall 40 with outward projections 48 of the filtering needle cap 14. The resulting interference fit retains the filter element 32 to the outer wall 40. The filter element 32 has an outer diameter DD corresponding to that of the intermediate portion 30 as shown. Thus a filtering needle cap 14 with an engaged filter element 32 will have a substantially similar outside diameter DD both proximal and distal of the shoulder 72.

The distal portion 26 of the filtering needle cap 14 may have a smooth cylindrical inner wall 42.

A sealing sleeve 50 is secured within the inner wall 52 of the filtering needle cap 14 near the distal portion 26 end by suitable barbs or detents 54. As noted in the alternatives and variation section of this disclosure, there are many different ways to connect the various components and the body of the disclosure will tend to give a single example with the knowledge that those of skill in the art can use a wide range of techniques to connect components.

The sealing sleeve 50 has a cylindrical central opening defined by inner wall 58 sized for receiving the needle 36 therein. When the needle 36 is positioned coaxially within the filtering needle cap 14, as shown in FIG. 2 and FIG. 4, the distal end 38 of the needle 36 engages the inner wall 58 of the sealing sleeve 50 forming a chamber 60 defined by:

A chamber end 76 of the filter element 32,
The inner wall 42 of the distal portion 26 of the filtering needle cap 14; and
A distal end 74 the end of the sealing sleeve 50.

The inner diameter of the inner walls 58 may be less than the outer diameter of the needle 36 until the needle 36 is inserted through the sealing sleeve 50 to form an interference fit.

The distal end 38 of the needle 36 may be formed with a sharp point as shown in the various drawings of this disclosure. As discussed below, other distal ends including blunt points may be used.

The distal end 38 of the needle extends beyond the sealing sleeve 50 into the chamber 60 so that opening 56 may intake liquid payload when the syringe is operated. When designing a filtered needle 10, one design criteria is to minimize the dead volume. Dead volume is the volume of liquid payload that is drawn in into the filtering needle cap 14 but does not enter the opening 56 of the needle 36. The liquid payload between the opening 56 and the distal end of the filtering needle cap 14 is discarded when the filtering needle cap 14 is discarded. While some loss of liquid payload is unavoidable as some liquid payload will be within the filter element 32, minimizing dead volume remains desirable. Placing the distal end of the sealing sleeve 50 near the opening 56 of the needle 36 helps minimize the dead volume. Placing the opening 56 of the needle 36 near the proximal end of the filter element 32 helps minimize the dead volume. Using a reduced bore size on the proximal side of the filter element 32 helps minimize the dead volume.

Process for Use.

Figure 25:
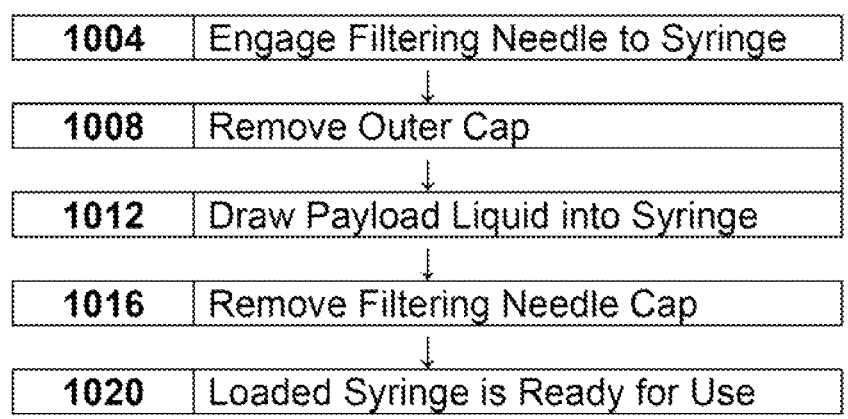
FIG. 25 illustrates process for use of a filtered needle.

FIG. 25 illustrates process 1000 for loading a filtered needle 10.

Step 1004—Engage Filtered Needle. The filtered needle 10 such as shown in FIG. 2 is secured to the end of a syringe (not shown) or other fitting by engagement with the hub 78 at the proximal end 34 of the needle and connector portion 16.

Step 1008—Remove Outer Cap. The outer cap 12 is removed. Note this step is optional as in some instances the filter needle may be delivered in sterile packaging such as a blister pack without an outer cap. In many instances the filter needle will be delivered with the needle and connector portion 16 factory inserted into the filtering needle cap 14 and with the outer cap 12 covering a portion of the filtering needle cap 14. In order to minimize the chances that the filtering needle cap 14 will be separated from the needle and connector portion 16 when intending to merely remove the outer cap 12, the components may be designed so that the force needed to remove the filtering needle cap 14 from the needle and connector portion 16 may be significantly more than the force needed to remove the outer cap 12 from the filtering needle cap 14. In this context, significantly more would include at least double. The difference in required force may be achieved by having different degrees of interference fits, or use of different materials or surface treatments. Other ways of increasing or decreasing the requisite removal force will be apparent to those of skill in the art.

Step 1012—Draw Payload into Syringe. The filter element 32 is immersed in an ampoule or suitable receptacle for a liquid payload such as a pharmaceutical or other liquid. As the syringe plunger is withdrawn in a known manner, the liquid payload is drawn up in order to fill the syringe through a pathway through:

the filter element 32,
the chamber 60; and
the interior of the needle 36.

The suction force for drawing up the liquid payload is confined to the pathway by the sealing sleeve 50 which closes the chamber 60. The sealing sleeve 50 prevents the flow of air in a distal direction from entering the chamber 60 from the outer perimeter of the needle 36 such that the syringe may effectively draw in liquid payload. As the syringe is loaded, any debris in the receptacle of liquid payload drawn up in the pharmaceutical is trapped in the filter element 32.

Step 1016—Remove Filtering Needle Cap. Once the syringe is loaded, the filtering needle cap 14 is removed from the needle and connector portion 16 by sliding the filtering needle cap 14 off the distal end 38 of the needle 36. The filtering needle cap 14 may then be discarded along with any debris captured in the filter element 32.

Step 1020—Loaded Syringe is Ready for Use. The syringe is loaded with the desired amount of liquid payload which has been filtered as the liquid passed through filter element 32. The distal end 38 of the needle 36 is exposed and ready for use. Depending on the application, the distal end 38 of the needle 36 may be inserted as appropriate into a patient's body; to a port with a septum for use with IV therapy, or some other location.

In order to appreciate the benefits of the process for using the various disclosed filter needles discussed in this disclosure, it is useful to review the prior two-step process. In the two stage process, a needle or straw has a filter element secured in the needle and connector portion. As the liquid payload is drawn up into the syringe, the filter traps the debris removing it from the liquid payload to be administered. The filtered straw or needle is then removed from the syringe and discarded.

Thus, after the liquid payload has been moved into the syringe, the syringe is disconnected from the filtered straw leaving the distal end of the syringe open and thus providing a path for bacterial contamination. A needle and connector portion is then connected to the distal end of the syringe and the liquid payload is now ready for delivery.

The present process connects the sterile needle and connector portion 16 with filtering needle cap 14 and optional outer cap 12 on the distal end of the syringe at the beginning of the process. The distal end of the syringe is not uncovered until after the delivery of the liquid payload to patient, IV port, or other desired delivery location. The removal of the filtered needle cap 14 unsheathes the distal end 38 of the needle 36 without any modification of the pre-existing engagement of the distal end of the syringe and the hub 78. The disclosed process has fewer steps and less chance for bacterial ingress into the assembly than the prior art two-step process with a filter straw.

FIG. 5 illustrates an alternative arrangement of a filter element 532 for filtered needle 510. The filter element 532 has a tail piece 564 on the proximal end of the filter element 532. The distal end 566 of the intermediate portion 530 of the filtering needle cap 514 is formed with a cylindrical opening 558 sized for closely receiving the tail piece 564 of the filter element 532. Inward projections 570 projecting into the cylindrical opening 558 engage the outer wall of the tail piece 564 to secure the filter element 532 to the filtering needle cap 514 as shown. The filter element 532 has a shoulder 536 to abut the distal end 526 of the filtering needle cap 514 so that the diameter of the filter element 532 substantially matches the outer diameter of the distal end 526 of the filtering needle cap 514. A chamber 560 is formed proximal relative to the tail piece 564 of the filter element 532 so that the only liquid that reaches the opening 56 of the needle 36 has been filtered of debris.

FIG. 6 through FIG. 9 illustrates another embodiment wherein reference numbers corresponding to similar features in FIG. 1 through FIG. 5 and are not further described. As shown in FIG. 6, filtered needle 610 has needle and connector portion 16, outer cap 12, and filter element 32 that may correspond to the items described above. The filtering needle cap 614 differs from the filtering needle cap 14 described above.

Figure 8:
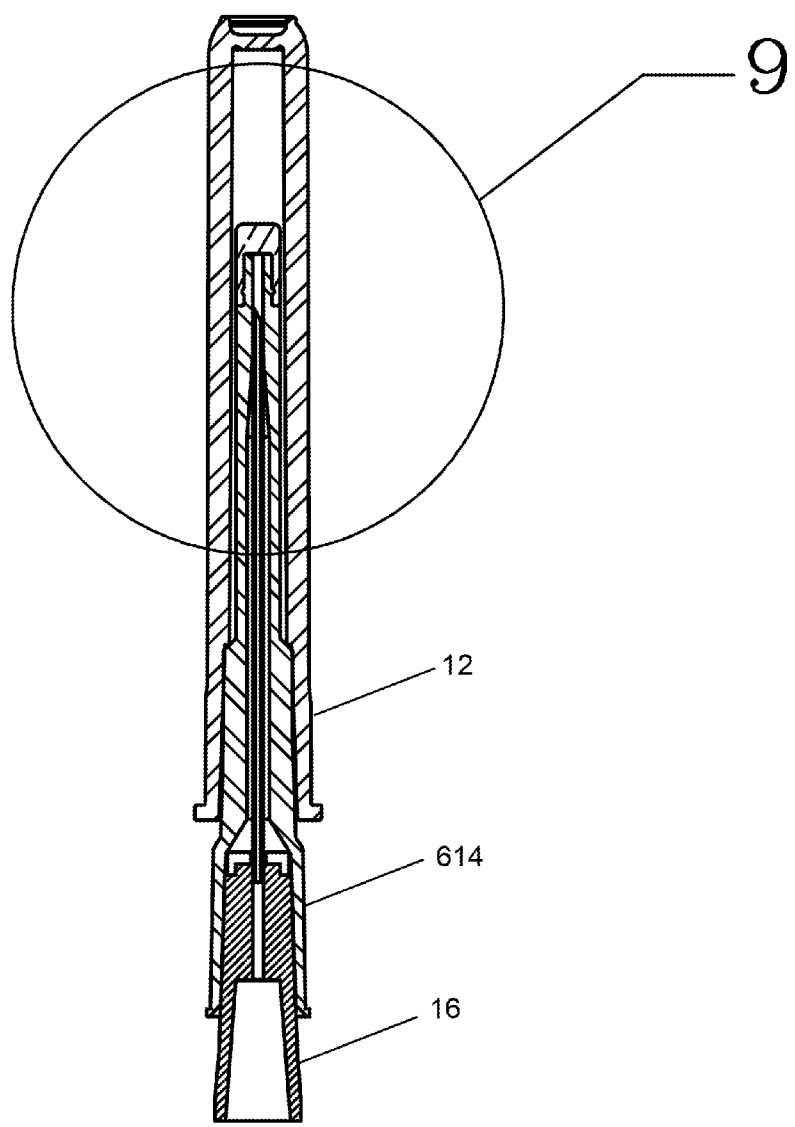
FIG. 8 is a sectional drawing taken along line 8-8 of FIG. 7.

FIG. 8 shows the assembled filtered needle 610 with the needle and connector portion 16 inserted into the filtering needle cap 614 which is inserted into the outer cap 12. FIG. 8 is a cross section of FIG. 7 and shows the portion of FIG. 8 shown in enlarged detail in FIG. 9.

Figure 9:
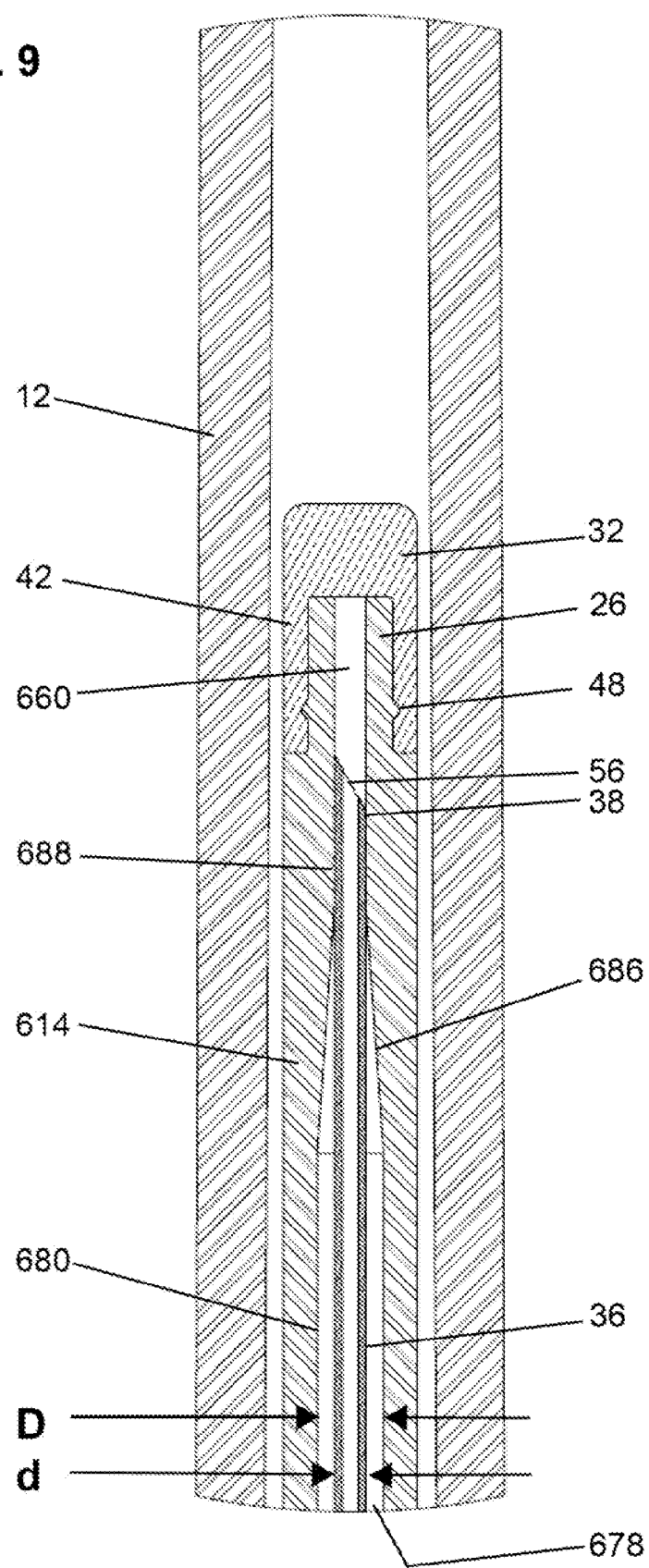
FIG. 9 is an enlargement of an alternative embodiment of a seal for the filter tip within circular arrow 9 shown in FIG. 8.

As best seen in FIG. 9, the filter element 32 is retained on the distal portion 26 of the filtering needle cap 614 by outward projections 48. Rather than having a sealing sleeve 50 as discussed above, filtering needle cap 614 has an interior channel 678 which tapers in a tapering section 686 from a first section 680 having diameter D to a second section 688 with a reduced inner diameter. Inner diameter D is larger than the outer diameter d of the needle 36. In contrast the diameter of second section 688 receives the distal end 38 of the needle 36 to form an interference fit to substantially seal the interior channel 678. As the distal end 38 of the needle 36 is inserted into the filtering needle cap 614, the needle seals the chamber 660 defined by the distal portion 26 of the filtering needle cap 614 and the filter element 32. Liquid payload is filtered while passing through the filter element 32 before reaching the opening 56 in the distal end 38 of the needle 36.

In the arrangement, the filtering needle cap 614 may be formed of a rigid material sized to closely fit or interfere with the outer diameter of the needle 36 so as to form the seal. Alternatively, the filtering needle cap 614 may be formed of a flexible material and the needle 36 may have a diameter which is larger than the inner diameter of the second section 688 causing the filtering needle cap 614 to deform as the distal end 38 of the needle 36 is inserted to form a seal.

Figure 10:
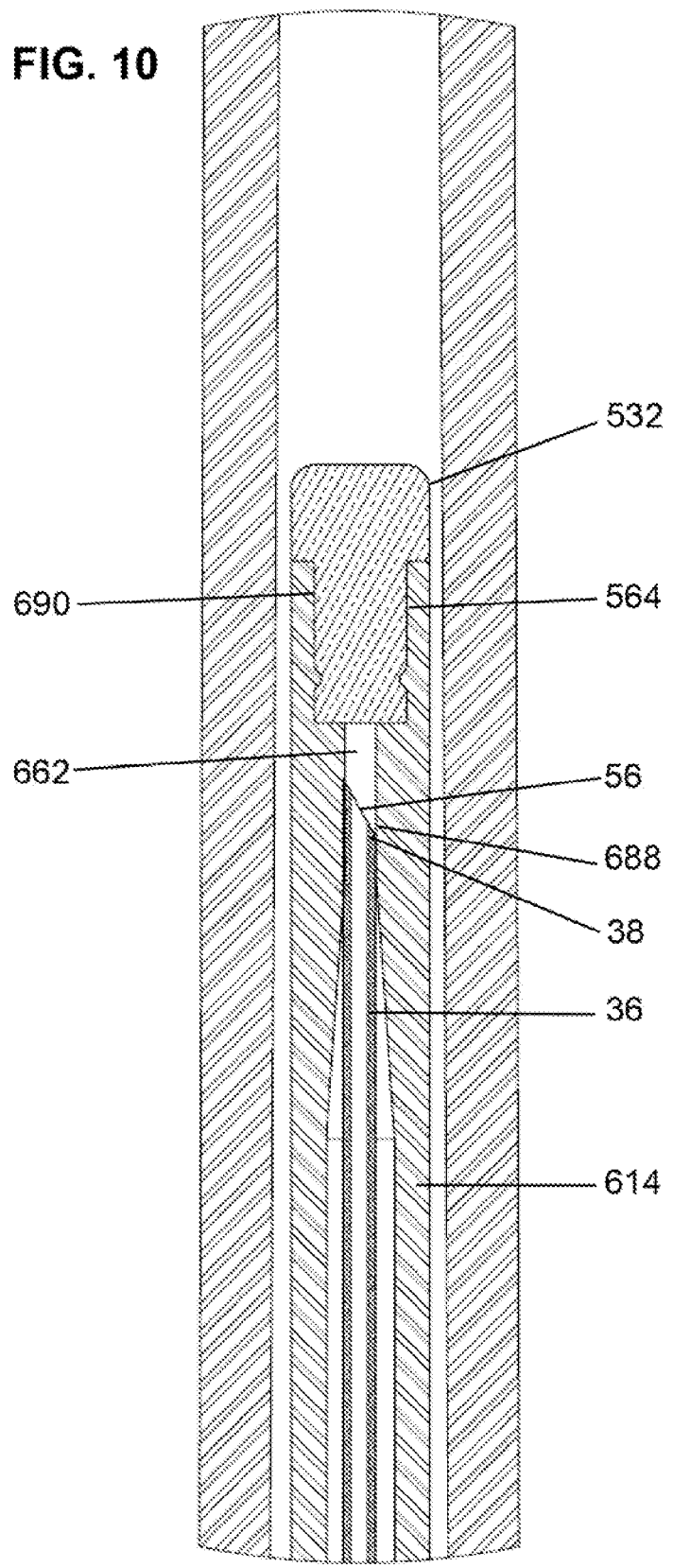
FIG. 10 is a fragmentary enlargement of an alternative embodiment of the filtering needle cap shown in FIG. 9.

FIG. 10 is similar to the arrangement of FIG. 9 except that in the latter, the filter element 532 with tail piece 564 discussed in connection with FIG. 5 is used to seal a distal portion 690 of filtering needle cap 614 which is has the relationship between the distal end 38 of the needle 36 with the second section 688 described above. Liquid payload drawn through the filter element 532 passes through chamber 662 into the opening 56 at the distal end 38 of the needle 36.

FIG. 11 through FIG. 14 illustrate an arrangement of an embodiment of a filtered needle 710 with outer cap 712 and needle and connector portion 16 having a needle 36 with distal end 38. Filtered needle 710 includes needle cap 714, filter element 732, and sleeve 708.

Figure 13:
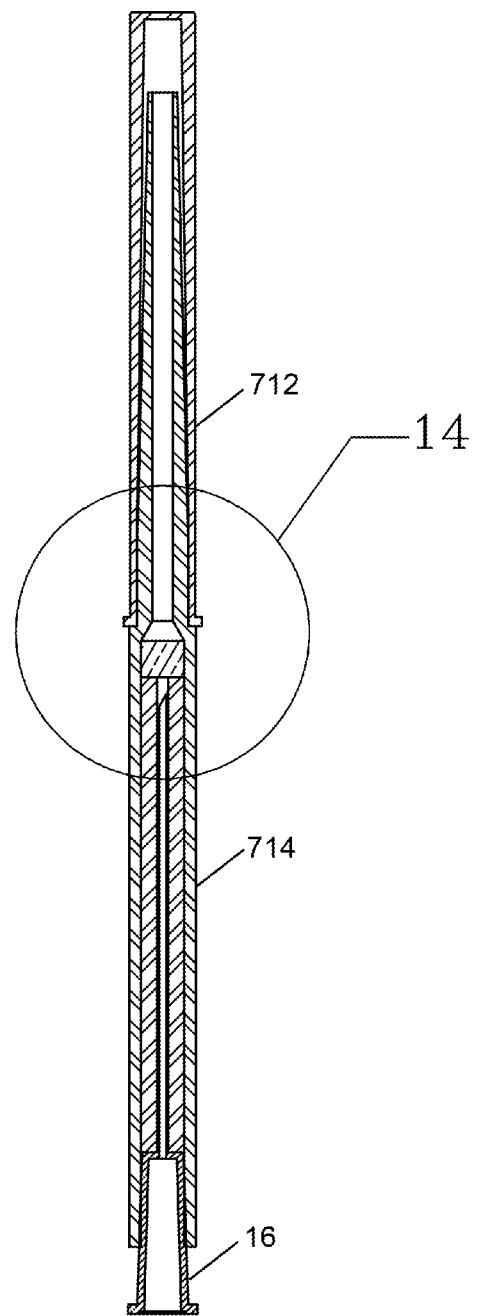
FIG. 13 is a sectional illustration of the filtering needle cap taken along line 13-13 of FIG. 12.

FIG. 12 shows an assembled filtered needle 710. FIG. 13 shows a cross section for FIG. 12 and indicates the region of FIG. 13 shown in enlarged detail in FIG. 14.

Turning now to FIG. 14, when the filtered needle 710 is assembled, the needle 36 is surrounded by sleeve 708. A filter element 732 is positioned distal to the sleeve 708 and proximal to a frusta-conical segment 720 of the interior bore of the needle cap 714 that transitions from the larger diameter portion 724 of the needle cap 714 to the smaller diameter portion 728 of the needle cap 714. The filter element 732 may be force fit to abut the frusta-conical segment 720 as shown, or the filter element 732 may be held with detents, not shown, or the filter element 732 may be held in position by an adhesive. The sleeve 708 may likewise be held in position by adhesives, detents or a force fit.

The needle 36 is fit into an inner channel 740 within the sleeve 708 to form a seal between the needle 36 and the sleeve 708. When the filtered needle 710 is assembled, the sharp distal end 38 of the needle 36 is positioned proximal relative to the filter element 732 separated by a small chamber 736.

When a connected syringe (not shown) draws a liquid payload through the distal tip of the filtered needle 710, the liquid payload passes through the smaller diameter portion 728, the frusta-conical segment 720, the filter element 732, the small chamber 736, and into an opening 56 in the distal end 38 of the needle 36.

In the arrangement illustrated the needle cap 714 may be formed of a flexible material which is sized so that the distal end 744 (FIG. 11) thereof may be immersed in an open ampoule for drawing up fluids through the filter element 732, thus trapping debris. When the liquid is drawn up, the needle cap 714 may be separated from the needle and connector portion 16 and discarded. The needle and connector portion 16 with the needle 36 may thereafter by employed to administer the filtered liquid to the patient either directly or indirectly through an IV.

The seal formed between the needle 36 and the sleeve 708 advantageously shields the outer surface of the needle 36 from exposure to liquids. The small chamber 736 desirably limits the volume of liquid which may be wasted when it is drawn up by the syringe as the contents of the small chamber 736 are discarded with the needle cap 714.

FIG. 15 through FIG. 18 illustrate an embodiment of a filtered needle 810. FIG. 15 is an exploded diagram with outer cap 812, filtering needle cap 814, filter element 832, sleeve 808, and needle and connector portion 16 with needle 36 and distal end 38. FIG. 16 is a view of an assembled filtered needle 810. FIG. 17 is a cross section of FIG. 16 and identifies the region of FIG. 16 that is shown in enlarged detail in FIG. 18.

Figure 18:
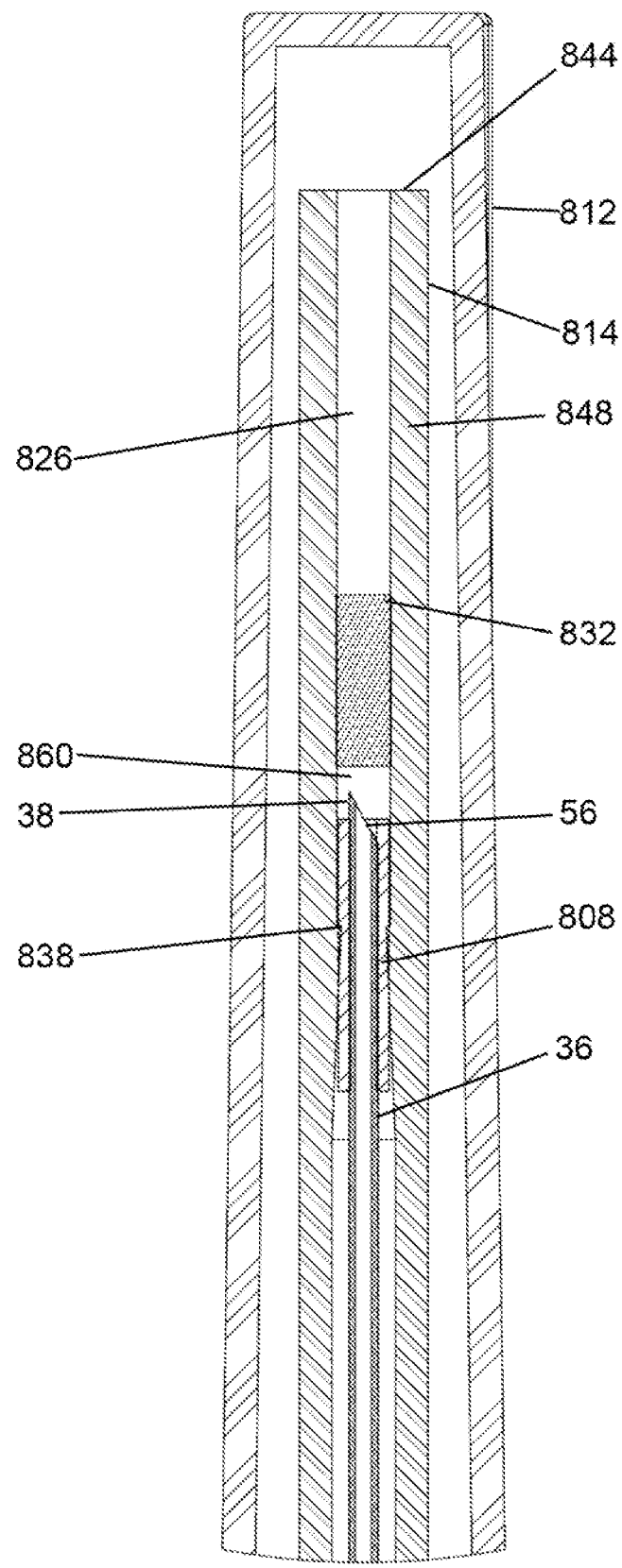
FIG. 18 is a fragmentary enlargement of the filter tip within circular arrow 18 shown in FIG. 17.

Turning now to FIG. 18, the filtering needle cap 814 is formed with an elongated straw portion 848 having uniform outer diameter and an interior passageway 826, likewise has a uniform diameter. A filter element 832 is located in the interior passageway 826 distal to the distal end 38 of the needle 36. The sleeve 808 fills the gap between the outer diameter of the needle 36 and the inner diameter of the interior passageway 826 to form a seal. The sleeve 808 may be held in position by inward protrusions 838, adhesives, or an interference fit. A small chamber 860 exists between the proximal end of the filter element 832 and the distal end 38 of the needle 36.

The sleeve 808 may be rigid and rely on close tolerances for an interference fit with the needle 36 or the sleeve 808 may be elastically deformable. After removing the outer cap 812, a syringe may draw liquid payload through the distal end 844 of the filtering needle cap 814, through the filter element 832, the small chamber 860, and into the opening 56 in the distal end 38 of the needle 36.

Figure 19:
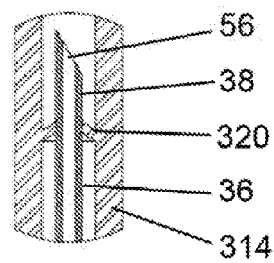
FIG. 19 is a fragmentary sectional view of a filtering needle cap according to another embodiment which uses an annular seal.

FIG. 19 shows a fragmentary detail of a filtered needle 310 with filtering needle cap 314. Visible in FIG. 19 is the distal end 38 of needle 36 extending through sealing annulus 320. The sealing annulus 320 is sized to have an open bore with a diameter smaller than the outer diameter of the needle 36. The sealing annulus 320 may have a taper on the inner bore to facilitate lead in as the needle 36 is moved distally. As the distal end 38 of the needle 36 is inserted through the sealing annulus 320, a seal is formed and the inner diameter of the sealing annulus 320 will tend to move distally during the deformation of the sealing annulus 320. The sealing annulus 320 may be formed initially with the inner diameter of the sealing annulus 320 distal relative to the connection of the outer diameter of the sealing annulus 320 and the inner wall of the filtering needle cap 314. The seal formed by the insertion of the needle 36 does not need to be perfect, just sufficient to allow a syringe to draw liquid payload through the opening 56 in the distal end 38 of the needle 36 after the liquid payload has passed through the filter element (not shown here).

FIG. 20 depicts a filtered needle 410 similar to the arrangement shown in FIG. 18, except that the straw portion 848 from FIG. 18 is replaced with a two-part straw 404 having an interior channel 422. The two-part straw 404 has a proximal portion 418 and a mating distal portion 414 having an overlapping region 450. A sleeve 452 having a cylindrical through opening is disposed within the interior channel 422 bridging the overlapping region 450 securing the proximal portion 418 and the distal portion 414 together. A filter element 432 is located in the interior channel 422 above the overlapping region 450 as shown. The needle 36 extends through the distal end of the sleeve 452 into a small chamber 456 formed between the filter element 432, the distal end of the sleeve 452 and the space between the outside diameter of the needle 36 and the inside diameter of the distal portion 414 of the two-part straw 404. The proximal portion 418 of the two-part straw 404 may be formed of a rigid material; and the distal portion 414 of the two-part straw 404 may be formed of a flexible material to facilitate the drawing up of liquid from an ampoule or other liquid reservoir. Thus, the distal portion 414 may include a highly flexible portion such as tubing to facilitate the insertion into a reservoir to draw in liquid payload including liquid payload in a portion of the liquid reservoir not directly aligned with an opening to the liquid reservoir. Thus, the liquid payload may travel through a non-linear path through tubing bent to access the liquid payload in the liquid reservoir.

FIG. 21 through FIG. 24 illustrates a filtered needle 910. FIG. 21 is an exploded diagram showing an outer cap 912, a filtering needle cap 914 and a needle and connector portion 16. Visible within FIG. 21 within the filtering needle cap 914 are filter element 932, which fits into filter chamber 936 that is formed by open areas within proximal flange 974 and distal flange 976, and a straw 968.

Figure 22:
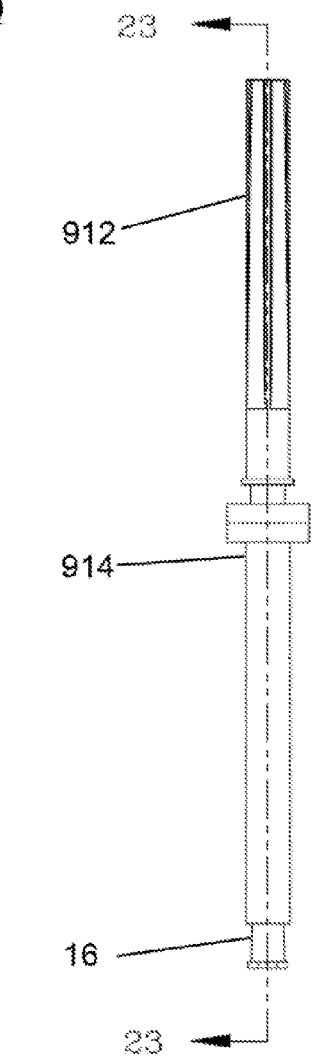
FIG. 22 is an elevation of the arrangement of FIG. 21 in assembled form.
Figure 23:
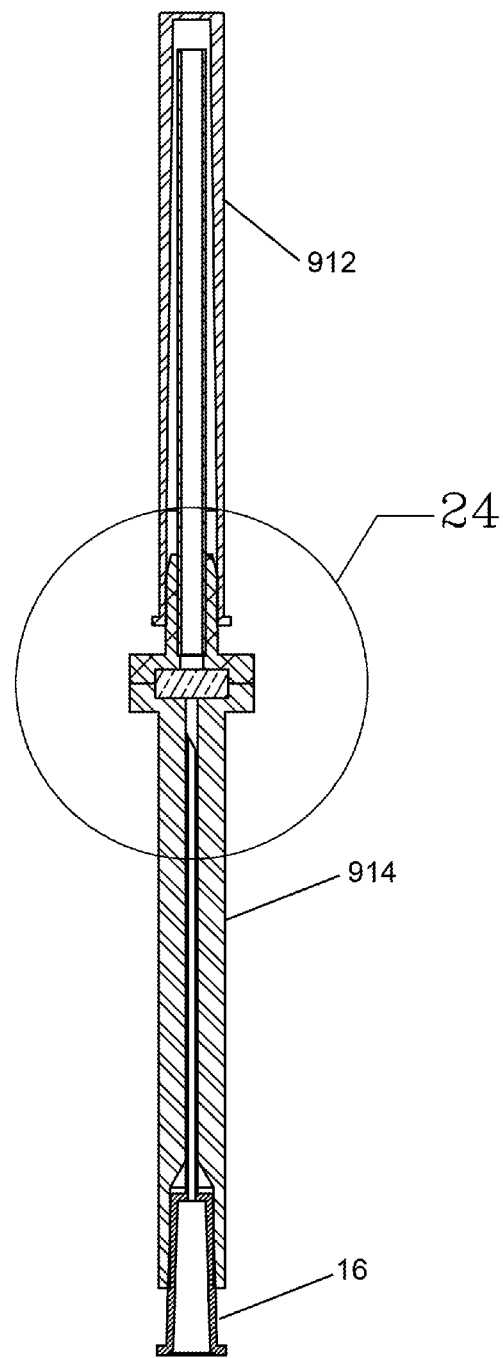
FIG. 23 is a sectional illustration of the filtering needle cap taken along line 23-23 of FIG. 22.

FIG. 22 shows an assembled filtered needle 910 with outer cap 912, filtering needle cap 914, and needle and connector portion 16. FIG. 23 shows a cross section of FIG. 22. FIG. 23 shows the circled area that is enlarged in FIG. 24.

Figure 24:
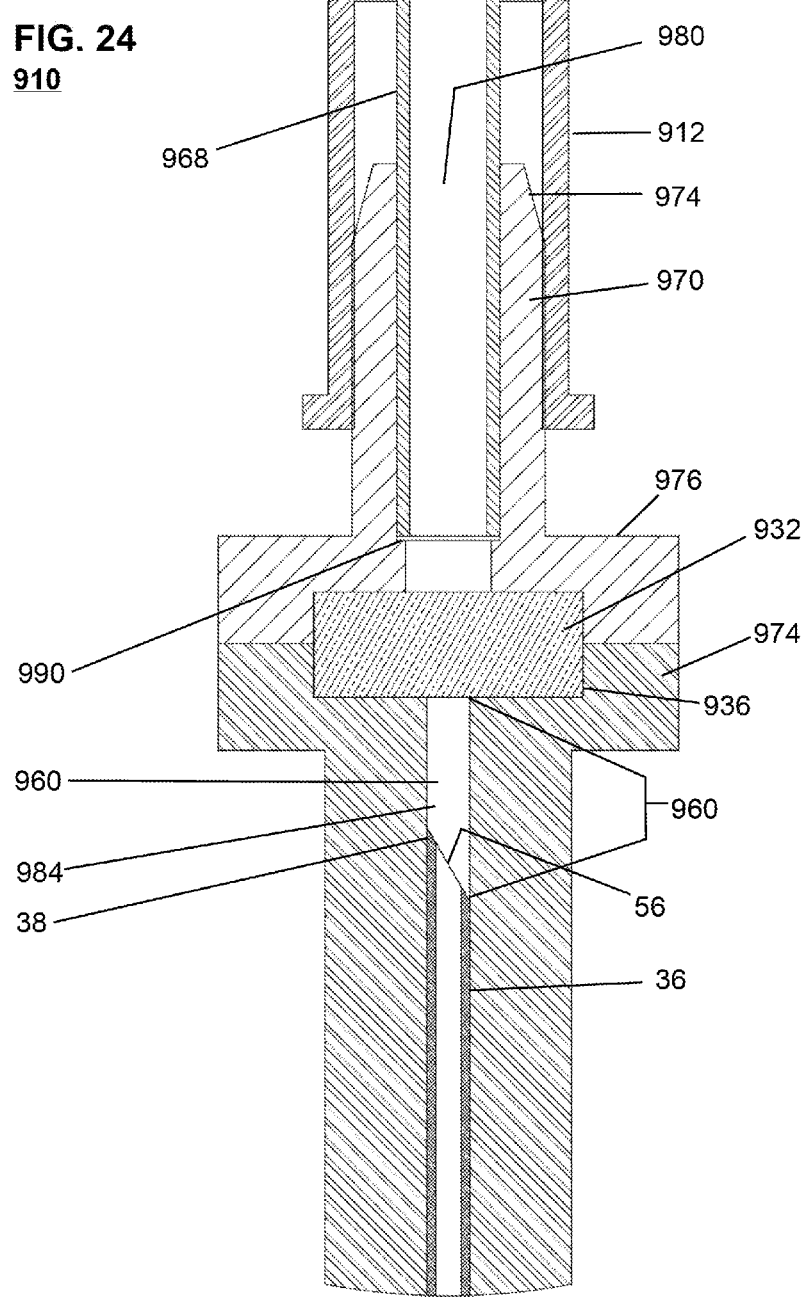
FIG. 24 is a fragmentary enlargement of the filter tip within circular arrow 24 shown in FIG. 23.

In FIG. 24 the filter element 932 is located in the filter chamber 936 that is located between a flanged face of the distal flange 976 and flanged face of the proximal flange 974. One of ordinary skill in the art will recognize that the proximal flange 974 or the distal flange 976 could be made deeper and the filter chamber 936 could be placed entirely in one flange rather than split between the proximal flange 974 and the distal flange 976. Distal expansion area 996 and proximal expansion area 998 increase the wetting area of the filter element 932 to increase the amount of debris that may be removed without materially affecting the ability to intake liquid payload across the filter. The increased wetting area also decreases the pressure drop across the filter element 932.

The straw 968 may be inserted into a distal bore 980 in a cylindrical portion 970 connected to the distal flange 976. A shoulder 990 may be used to limit the insertion depth of the straw 968. The cylindrical portion 970 may have a leading taper 994 to assist in placement of the outer cap 912.

As discussed above, the distal end 38 of the needle 36 and proximal bore 984 may be sized so that the needle 36 substantially seals the perimeter of the proximal bore 984. Liquid payloads may be drawn by a syringe through the straw 968, through the filter element 932 in the filter chamber 936 and into a proximal chamber 960 before entering opening 56 in the distal end 38 of the needle 36.

One of skill in the art will appreciate that the seal formed between the outer perimeter of the needle 36 and the proximal bore 984 does not need to be perfect as the opening 56 into the needle 36 provides a path of relatively low resistance for fluid flow.

Details

Choice of Filter Element.

One design criteria for choice of a filter element on the distal end of the filtering needle cap versus a filter element contained internal in the filtering needle cap is whether collection of abnormal components within the liquid payload is relevant to the application. While all filter elements may be used to remove shards of glass, in some instances it may be useful to use a filter element on the distal end of the filtering needle cap as this distal surface will concentrate certain types of abnormal components. For example, some pharmaceuticals may partially crystalize from age or handling. While a small amount of crystallization may be tolerated, an unusual amount of crystallization may indicate that the pharmaceutical should be discarded rather than used. Likewise, some pharmaceuticals may have a small amount of sediment in the reservoir of the pharmaceutical such as an ampoule, but if a large amount of sediment appears on the outer surface of the filter element, the excessive sediment may indicate that the pharmaceutical is too old or has been compromised by handling.

The filter elements may be sintered filters which have a number of tortuous internal channels for liquid payload to traverse while capturing debris. Extending the thickness of the filter increases the distance that the liquid payload must travel but it also increases the number of possible paths for the liquid payload to travel. Thus, for some range of thicknesses, increasing the thickness decreases the overall resistance to flow.

One well-known vendor in the field of sintered filter material is the Porex Corporation located in Fairburn Ga. and at www.porex.com.

Alternatives and Variations.

Retention of the Filter Element.

In some of the examples set forth above, the filter element was retained by protrusions or detents that extended into the filter element to secure the filter element. Adhesives may be used to secure the filter element. Many designers may prefer a protrusion or other form of interference fit as the use of adhesives might cause adhesives to enter possible flow paths for liquid payload and thus partially impair the filter element. Those of skill in the art will recognize that other attachment methods may be used such at an ultrasonic bond, spin welding, heat welding, and press fit. Likewise, other suggested connections between components have been provided to provide a suitable example and those of skill in the art will recognize the many options for connecting two components together. The teachings of this present disclosure are not limited to any particular connection method for joining components unless specifically recited in the claims that follow.

Needle Types.

The various figures discussed in connection with this disclosure have uniformly shown sharp distal ends for the needles. Sharp ended hypodermic needles are particularly adapted for injecting fluids directly into the body of the patient.

In many instances, the liquid payload is not delivered directly into the patient but is instead delivered to a bag of fluids used in intravenous therapy (IV therapy). A drip of liquid is provided into a vein of the patient to slowly provide a desired treatment. The IV fluids are typically in a bag. Ports with a self-sealing septum may be used to add pharmaceuticals to the liquid being provided in IV therapy. While a sharp tipped needle may be used to deliver a liquid payload through a septum, some prefer using a blunt tip needle. A blunt tip needle reduces the risk of a needle stick to the medical personnel and may be less damaging to the septum. While the variation of needle tips and the best uses for each type of needle tip is beyond the scope of the present disclosure, nothing in this present disclosure limits the teachings to applications with sharp point needles. Blunt tip needles will have openings on their distal portions and one of skill in the art can adapt the geometries of the filtering needle cap if needed to accommodate the geometry of various types of blunt tip needles.

Connection to the Hub.

The examples in this disclosure referenced a distal end of a syringe engaging with the hub 78. This may be the most common interaction with the filter needle, but the teachings of this disclosure could be employed where there is a combination of components rather than a syringe. For some specific reasons, there may be a series of components including check-valves, tubing, a syringe, or even a replacement for a syringe that may controllably intake and discharge liquid payload through the needle. The present disclosure may be used as long as there is an appropriate connection between the filtered needle and the remaining components via the distal fluid fitting of the remaining components.

Sterilization Choices.

Those of skill in the art will recognize that the filtering needle cap with our without an outer cap may be sterilized prior to provision to the medical facility. Those of skill in the art will recognize that there are many different processes such as electron beam processing, gamma ray sterilization, or ethylene oxide gas. Those of skill in the art will recognize that medical devices may be adapted for use with a particular sterilization process to maximize effectiveness and throughput. The teachings of the present disclosure may be adapted for use with a variety of sterilization techniques and thus this aspect of the examples was not highlighted or discussed.

Optional Use of Outer Cap.

As noted above, some applications may not use the outer cap but package the needle and connector portion along with the filtering needle cap in packaging such as a blister pack. The packaging would maintain the sterility of the items and would preclude even sterilized debris from becoming entrained in the filtering needle cap.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A filtered needle for use in administering a liquid payload, the filtered needle comprising: a connector portion and a filtering needle cap:
   the connector portion comprising:
      a hollow needle with a distal end of the hollow needle having an opening to a lumen running through the hollow needle; and
      a hub comprising:
         an open proximal end adapted to reversibly engage a fluid fitting; and
         a distal end of the hub engaged with a proximal end of the hollow needle; and
   the filtering needle cap comprising:
      a distal open end in fluid communication via an internal channel with a proximal open end of the filtering needle cap;
      the proximal open end of the filtering needle cap sized to receive the distal end of the hub within the proximal open end of the filtering needle cap to reversibly engage the hub when the distal end of the hollow needle is inserted into the internal channel,
      a filter element adapted for removing debris from the liquid payload as the liquid payload is drawn through the filtering needle cap into the lumen within the hollow needle as the liquid payload is drawn into the fluid fitting; and
      a sleeve to surround the distal end of the hollow needle to form a seal between the sleeve and the distal end of the hollow needle so that the liquid payload is drawn into the lumen in the hollow needle as the liquid payload is drawn into the fluid fitting and is blocked by the sleeve from traveling down an outside diameter of the hollow needle within the filtering needle cap.

2. The filtered needle of claim 1 wherein the distal end of the hollow needle has an outer diameter D and a distance between a proximal end of the filter element and the distal end of the hollow needle is within an order of magnitude of D.

3. The filtered needle of claim 1 further comprising an outer cap with a closed distal end which may be placed over at least a portion of the filtering needle cap until the filtered needle is uncovered for filtering the liquid payload as the liquid payload is drawn into the fluid fitting.

4. The filtered needle of claim 3 wherein the open proximal end of the hub is adapted to be reversibly engaged with the fluid fitting on a distal end of a syringe such that:
   operation of the syringe to intake the liquid payload through the hollow needle allows intake of the liquid payload that is filtered by the filter element; and
   subsequent removal of the filtering needle cap to expose the distal end of the hollow needle allows administration of a volume of filtered liquid payload through operation of the syringe.

5. The filtered needle of claim 1 wherein a portion of the filter element is a most distal portion of the filtering needle cap so that at least a portion of the filter element is inserted into a reservoir of the liquid payload to intake the liquid payload.

6. The filtered needle of claim 1 wherein the filter element is located between the distal open end and the proximal open end of the filtering needle cap.

7. The filtered needle of claim 6 where at least a portion of the filtering needle cap is sufficiently flexible to form a path with a non-linear centerline to allow the liquid payload to travel a non-linear path between the distal open end of the filtering needle cap and the filter element.

8. The filtered needle of claim 1 wherein the fluid fitting is a type of Luer fitting.

9. The filtered needle of claim 1 wherein the hub is engaged with the proximal end of the hollow needle via an adhesive element.

10. The filtered needle of claim 1 provided in a kit with a reservoir of the liquid payload for administration to a patient using the hollow needle after the liquid payload has been filtered.

11. A method for loading a quantity of a filtered liquid payload into a syringe and a connected hollow needle, the method comprising:
   obtaining a reservoir of a liquid payload;
   obtaining the syringe attached to a filtered needle, the filtered needle comprising: a connector portion and a filtering needle cap:
   the connector portion comprising:
      a hollow needle with a distal end of the hollow needle having an opening to a lumen running through the hollow needle; and
      a hub comprising:
         an open proximal end adapted to reversibly engage a fluid fitting; and
         a distal end of the hub engaged with a proximal end of the hollow needle; and
   the filtering needle cap comprising:
      a distal open end in fluid communication via an internal channel with a proximal open end of the filtering needle cap;
      the proximal open end of the filtering needle cap sized to receive the distal end of the hub within the proximal open end of the filtering needle cap to reversibly engage the hub when the distal end of the hollow needle is inserted into the internal channel,
      a filter element adapted for removing debris from the liquid payload as the liquid payload is drawn through the filtering needle cap into the lumen within the hollow needle as the liquid payload is drawn into the fluid fitting; and
      a sleeve to surround the distal end of the hollow needle to form a seal between the sleeve and the distal end of the hollow needle so that the liquid payload is drawn into the lumen in the hollow needle as the liquid payload is drawn into the fluid fitting and is blocked by the sleeve from traveling down an outside diameter of the hollow needle within the filtering needle cap;

using the syringe to draw in the liquid payload from the reservoir of the liquid payload, the liquid payload passing through the filter element before entering the opening in the distal end of the hollow needle; and removing the filtering needle cap from the filtered needle to expose the distal end of the hollow needle.

12. The method of claim 11 wherein the distal end of the hollow needle has an outer diameter D and a distance between a proximal end of the filter element and the distal end of the hollow needle is within an order of magnitude of D.

13. The method of claim 11 wherein the syringe draws the liquid payload through the filter element before the liquid payload enters an interior channel within the filtering needle cap.

14. The method of claim 11 wherein the syringe draws the liquid payload into the distal open end of the filtering needle cap before passing through the filter element.

15. The method of claim 11 wherein the step of obtaining the syringe attached to the filtered needle comprises:
   obtaining the filtered needle;
   obtaining the syringe; and
   engaging a distal end of the syringe with a proximal end of the filtered needle.

16. The method of claim 11 wherein the syringe remains connected to the hub continuously from before the syringe is used to draw in the filtered liquid payload through the filter element until after the syringe is used to deliver at least a portion of the liquid payload to a destination.

17. The method of claim 11 wherein the filtered needle is initially sheathed in an outer cap and a force required to remove the outer cap from the filtering needle cap is less than half of a force needed for removing the filtering needle cap from the filtered needle to expose the distal end of the hollow needle.

18. The method of claim 11 wherein the liquid payload is delivered through a septum for use in IV therapy.

\* \* \* \* \*

UNITED STATES PATENT AND TRADEMARK OFFICE
CERTIFICATE OF CORRECTION

Page 1 of 1

PATENT NO.       : 9,669,164 B2
APPLICATION NO.  : 14/942876
DATED            : June 6, 2017
INVENTOR(S)      : Carr et al.

It is certified that error appears in the above-identified patent and that said Letters Patent is hereby corrected as shown below:

In the Claims

Column 16, Line 09, Claim 16, 'filtered liquid payload' should read -liquid payload-.

Column 16, Line 11, Claim 16, 'liquid payload' should read -filtered liquid payload-.

Signed and Sealed this
Fifteenth Day of January, 2019

Andrei Iancu
*Director of the United States Patent and Trademark Office*